United States Patent
McGraw, III

(10) Patent No.: US 10,610,519 B2
(45) Date of Patent: *Apr. 7, 2020

(54) METHODS AND COMPOSITIONS FOR TREATING HYPERHIDROSIS

(71) Applicant: THERAVIDA, INC., Durham, NC (US)

(72) Inventor: Benjamin F. McGraw, III, San Mateo, CA (US)

(73) Assignee: THERAVIDA, INC., San Mateo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/403,115

(22) Filed: May 3, 2019

(65) Prior Publication Data

US 2019/0307727 A1    Oct. 10, 2019

Related U.S. Application Data

(63) Continuation of application No. 15/456,414, filed on Mar. 10, 2017, now Pat. No. 10,328,057, which is a continuation of application No. PCT/US2016/014150, filed on Jan. 20, 2016.

(51) Int. Cl.

| | |
|---|---|
| *A61K 9/48* | (2006.01) |
| *A61K 9/50* | (2006.01) |
| *A61K 31/4178* | (2006.01) |
| *A61K 31/216* | (2006.01) |
| *A61K 9/16* | (2006.01) |

(52) U.S. Cl.
CPC ........ *A61K 31/4178* (2013.01); *A61K 9/1635* (2013.01); *A61K 9/1652* (2013.01); *A61K 9/5078* (2013.01); *A61K 9/5084* (2013.01); *A61K 31/216* (2013.01); *A61K 9/5047* (2013.01)

(58) Field of Classification Search
CPC .......................... A61K 9/5084; A61K 5/5084
See application file for complete search history.

(56) References Cited

U.S. PATENT DOCUMENTS

| | | |
|---|---|---|
| 4,209,505 A | 6/1980 | Mikhail |
| 4,302,440 A | 11/1981 | John et al. |
| 4,927,640 A | 5/1990 | Dahlinder et al. |
| 5,674,895 A | 10/1997 | Guittard et al. |
| 5,840,754 A | 11/1998 | Guittard et al. |
| 6,033,685 A | 3/2000 | Qiu et al. |
| 6,149,943 A | 11/2000 | McTeigue et al. |
| 6,419,954 B1 | 7/2002 | Chu et al. |
| 6,482,837 B1 | 11/2002 | Wood |
| 6,627,635 B2 | 9/2003 | Palermo et al. |
| 6,660,382 B2 | 12/2003 | Nouri et al. |
| 6,692,769 B1 | 2/2004 | Ishibashi et al. |
| 6,716,449 B2 | 4/2004 | Oshlack et al. |
| 6,787,156 B1 | 9/2004 | Bar-Shalom |
| 7,026,329 B2 | 4/2006 | Crain et al. |
| 7,419,686 B2 | 9/2008 | Kaiko et al. |
| 7,666,894 B2 | 2/2010 | Paborji |
| 7,678,821 B2 | 3/2010 | Paborji |
| 7,781,472 B2 | 8/2010 | Paborji |
| 7,897,179 B2 | 3/2011 | Mulye |
| 8,007,825 B2 | 8/2011 | Wynn et al. |
| 8,110,226 B2 | 2/2012 | Li |
| 8,470,864 B2 | 6/2013 | Paborji |
| 8,652,523 B2 | 2/2014 | Guimberteau et al. |
| 8,821,935 B2 | 9/2014 | Guimberteau et al. |
| 8,906,419 B2 | 12/2014 | Mulye |
| 8,940,763 B2 | 1/2015 | Paborji et al. |
| 9,132,124 B2 | 9/2015 | Paborji et al. |
| 9,415,013 B2 | 8/2016 | Paborji et al. |
| 9,744,157 B2 | 8/2017 | Paborji et al. |
| 9,968,556 B2 | 5/2018 | Paborji et al. |
| 10,328,057 B2 | 6/2019 | McGraw, III |
| 2004/0185111 A1 | 9/2004 | Rubino et al. |
| 2005/0287211 A1 | 12/2005 | Yoshida et al. |
| 2007/0053995 A1 | 3/2007 | Paborji |
| 2007/0077300 A1 | 4/2007 | Wynn et al. |
| 2007/0224269 A1 | 9/2007 | Rubino et al. |
| 2008/0207737 A1 | 8/2008 | Zinger et al. |
| 2008/0254115 A1 | 10/2008 | Rubino |
| 2008/0299393 A1 | 12/2008 | Wu |

(Continued)

FOREIGN PATENT DOCUMENTS

| | | |
|---|---|---|
| CN | 101287462 A | 10/2008 |
| EP | 1629834 A1 | 3/2006 |

(Continued)

OTHER PUBLICATIONS

"Pilocarpine". Drug Facts and Comparisons. 1996 Edition. pp. 2672-2675.

Aframian, D.J. et al., "Pilocarpine Treatment in a Mixed Cohort of Xerostomic Patients," Oral Diseases, (2007) 13:88-92.

ANZCTR (A Phase 2a Study Evaluating the Safety and Efficacy of THVD-102, a combination of Oxybutynin and Pilocarpine, in Subjects with Primary Focal Hyperhidrosis, Australian New Zealand Clinical trial registry, Mar. 2015, p. 1-6) (Year: 2015).

Anzctr Australian New Zealand Clinical Trials Registry, Clinical Trial Description; Jul. 21, 2015; "The Safety and Efficacy of THVD-102, a combination ofOxybutynin and Pilocarpine, in Subjects with Primary Focal Hyperhidrosis"; (website) 9 pages.

(Continued)

*Primary Examiner* — Kyle A Purdy

(74) *Attorney, Agent, or Firm* — Pepper Hamilton LLP

(57) ABSTRACT

Aspects of the disclosure include methods for treating hyperhidrosis in a subject with a composition including a muscarinic antagonist and a muscarinic agonist. In practicing methods according to certain embodiments, a therapeutically effective amount of a composition including a muscarinic antagonist or a pharmaceutically acceptable salt thereof and a muscarinic agonist or a pharmaceutically acceptable salt thereof is administered to a subject and is sufficient to reduce hyperhidrosis in the subject and to reduce a dry mouth side effect of the muscarinic antagonist. Compositions for practicing the subject methods are also described as well as dose units containing one or more of the subject compositions.

18 Claims, 10 Drawing Sheets

(56) References Cited

U.S. PATENT DOCUMENTS

| | | |
|---|---|---|
| 2009/0017111 A1 | 1/2009 | Van den Heuvel et al. |
| 2009/0192228 A1 | 7/2009 | Wang |
| 2009/0247628 A1 | 10/2009 | Gant et al. |
| 2009/0275629 A1 | 11/2009 | Paborji |
| 2009/0318522 A1 | 12/2009 | Paborji |
| 2010/0137392 A1 | 6/2010 | Paborji |
| 2010/0152263 A1 | 6/2010 | Paborji |
| 2011/0244051 A1 | 10/2011 | Paborji et al. |
| 2011/0245294 A1 | 10/2011 | Paborji et al. |
| 2012/0201894 A1 | 8/2012 | Paborji et al. |
| 2012/0289543 A1 | 11/2012 | Paborji et al. |
| 2012/0289544 A1 | 11/2012 | Paborji et al. |
| 2013/0289087 A1 | 10/2013 | Paborji |
| 2014/0037713 A1 | 2/2014 | Wotton et al. |
| 2014/0105976 A1 | 4/2014 | Paborji et al. |
| 2018/0243218 A1 | 8/2018 | Paborji et al. |

FOREIGN PATENT DOCUMENTS

| | | | |
|---|---|---|---|
| WO | 9405263 | A1 | 3/1994 |
| WO | 9709980 | A1 | 3/1997 |
| WO | 98042318 | A1 | 10/1998 |
| WO | 200119901 | A2 | 3/2001 |
| WO | 0134139 | A1 | 5/2001 |
| WO | 2001054728 | A1 | 8/2001 |
| WO | 2003013538 | A1 | 2/2003 |
| WO | 2003082207 | A2 | 10/2003 |
| WO | 2004105735 | A1 | 12/2004 |
| WO | 2005046684 | A1 | 5/2005 |
| WO | 2005123042 | A1 | 12/2005 |
| WO | 2006026556 | A2 | 3/2006 |
| WO | 2006132196 | A1 | 12/2006 |
| WO | 2007027675 | A1 | 3/2007 |
| WO | 2007029087 | A2 | 3/2007 |
| WO | 2007041367 | A2 | 4/2007 |
| WO | 2009019599 | A2 | 2/2009 |
| WO | 2009022354 | A2 | 2/2009 |
| WO | 2009045796 | A1 | 4/2009 |
| WO | 2009057138 | A2 | 5/2009 |
| WO | 2011123815 | A1 | 10/2011 |
| WO | 2011123836 | A2 | 10/2011 |
| WO | 2012154770 | A1 | 11/2012 |

OTHER PUBLICATIONS

Aromdee, Chantana et al., "A Pilot Study of the Disposition of Pilocarpine in Plasma, Saliva and Urine After a Single Oral Dose," European Journal of Pharmaceutical Sciences, (1999) 8:81-83.

Boz JD (2015) "Systemic Treatment of Hyperhidrosis"; Actas Dermosifiliogr. 106(4); pp. 271-277.

Chancellor, Michael B. et al., "A Comparison of the Effects on Saliva Output of Oxybutynin Chloride and Tolterodine Tartrate," Clinical Therapeutics, (2001) 23:5:753-760.

Chapple Christopher R., "Muscarinic Receptor Antagonists in the Treatment of Overactive Bladder," Urology, 55(Supplement 5A), May 2000, 33-46.

Chapple, Christopher et al., "The Effects of Antimuscarinic Treatments in Overactive Bladder: A Systematic Review and Meta-Analysis," European Urology, (2005) 48:5-26.

Cheshire et al.; (2008) "Drug-induced hyperhidrosis and hypohidrosis: incidence, prevention and management"; Drug Safety 31 (2) :pp. 109-126.

Clemett, et al; (2001) "Tolterodine: a review of its use in the treatment of overactive bladder"; Drugs & Aging 18(4):277-304.

Detrol (R) Package Insert; Pfizer, Inc. Mar. 2008, 14 pgs.

Diokno, Ananias et al., "Prospective, Randomized, Double-Blind Study of the Efficacy and Tolerability of the Extended-Release Formulations of Oxybutynin and Tolterodine for Overactive Bladder: Results of the OPERA Trial," Mayo Clin Proc., (2003)78:687-695.

Eisai Inc. "Salagen: FDA Package Insert," Dec. 2009, 13 pages.

Foote, Jenelle et al., "Treatment of Overactive Bladder in the Older Patient: Pooled Analysis of Three Phase II Studies of Darifenacin, an M3 Selective Receptor Antagonist," European Urology, (2005) 48:471-477.

Gautam et al., "Cholinergic Stimulation of Salivary Secretion Studied with M.sub.1 and M.sub.3 Muscarinic Receptor Single- and Double-Knockout Mice"; Molecular Pharmacology, 66(2); 260-269 (Aug. 2004).

Harris, N.O. et al., (1960) "Infrared Spectral Characteristics of Pilocarpine-stimulated Saliva of Normally Caries-resistant Animals Compared with Caries-resistant and -susceptible Humans"; J. Dent. Res. 39:810-811.

Hornberger, J. et al. "Recognition, diagnosis, and treatment of primary focal hyperhidrosis"; J. Am. Acad. Dermatol. vol. 51, (Aug. 2004) pp. 274-286.

Humbert et al. (Use of oral oxybutynin at 7.5 mg per day in primary hyperhidrosis, Rev. Med. Liege, 2012, col. 67, pp. 520-526 and English Abstract) (Year: 2012).

International Preliminary Report on Patentability dated Apr. 16, 2007 in PCT/US2006/033671.

Iwabuchi et al. (Exploratory study on reduction of the incidence of hyperhidrosis by oral pilocarpine, J. Oral and Maxillofacial Surgery Medicine and Pathology, vol. 26, 2014, pp. 179-182) (Year: 2014).

Jacobs, CD, et al. (1996) "A multicenter maintenance study of oral pilocarpine tablets for radiation-induced xerostomia"; Oncology 10(3 Suppl); pp. 16-20.

Kim, W.O. et al. (2010) "Treatment of generalized hyperhidrosis with oxybutynin in post-menopausal patients"; Acta Derm Venereal. vol. 90; pp. 291-293.

Loscher, W. and Honack, D., "Withdrawal Precipitation by Benzodiazepine Receptor Antagonists in Dogs Chronically Treated with Diazepam or the Novel Anxiolytic and Anticonvulsant Beta-carboline Abecarnil," Naunyn Schmiedebergs Arch. Pharmacol. (1992), 345, 452-460.

MacDiarmid, Scott A. et al., "Efficacy and Safety of Extended Release Oxybutynin for the Treatment of Urge Incontinence: An Analysis of Data From 3 Flexible Dosing Studies," The Journal of Urology, (2005) 174:1301-1305.

Masters, Kim J., (2005) "Pilocarpine Treatement of Xerostmia Induced by Psychoactive Medications" American Journal of Psychiatry 162(5):1023.

Nagao, Mitsuhiro, et al. (1999) "Effects of propiverine hydrochloride (propiverine) on the muscarinic receptor binding affinity in guinea pig tissues and on salivation in conscious dogs"; Folia Pharmacologica Japonica, vol. 113, No. 3; pp. 157-166.

Oki, Tomomi et al., "Comparitive Evaluation of Exocrine Muscarinic Receptor Binding Characteristics and Inhibition of Salivation of Solifenacin in Mice," Biol. Pharm. Bull, (2006) 29(7):1397-1400.

Oki, Tomomi et al., "Demonstration of Bladder Selective Muscarinic Receptor Binding by Intravesical Oxybutynin to Treat Overactive Bladder," The Journal of Urology vol. 172: (2004): pp. 2059-2064.

Oki, Tomomi et al., "Muscarinic Receptor Binding, Plasma Concentration and Inhibition of Salivation After Oral Administration of a Novel Antimuscarinic Agent, Solifenacin Succinate in Mice," British Journal of Pharmacology, (2005) 145:219-227.

Olsson, et al. (2001) "Multiple dose pharmacokinetics of a new once daily extended release tolterodine formulation versus immediate release tolterodine"; Clin Pharmacokinet. 40(3):227-235.

Oxybutynin Chloride. Drug Facts & Comparisons, Urinary Tract Products, Dec. 1984, p. 730, Wolters Kluwer Health.

Paborji, M. et al: "Phase I Evaluation of THVD-201. A Fixed-Dose Combination of Tolterodine and Pilocarpine, to Eliminate the Dry Mouth Side Effect of Anti-Muscarinic Therapy for Overactive Bladder" European Urology Supplements, vol. 10. No. 2; Mar. 22, 2011; p. 277. XP008152710.

Pattee, et al. (1992) "Drug Treatment of the Irritable Bowel Syndrome"; Drugs, vol. 44, No. 2; pp. 200-206.

Physicians Desk Reference (PDR) (2002), pp. 229-2230.

Prescribing information for EMBEDA.TM., Jun. 2009, product information. 12 pages. Bristol, TN: King Pharmaceuticals, Inc.; https://www.accessdata.fda.gov/drugsatfda_docs/label/2009/022321s000lb1.pdf.

Product and Technology website [on-line]. Theravida, Inc. Mar. 9, 2015 (Mar. 9, 2015) [web archive retrieved on Mar. 10, 2016].

(56) References Cited

OTHER PUBLICATIONS

Retrieved from the Internet URL:—http://web.archive.org/web/20150309011535/htlp://theravida.com/product.html> andURL:http://web.archive.org/web/20 150309011557 /http:/ / theravida .com/technology .html>.

Rappaport, Bob A., NDA Approval letter for EMBEDA.TM., Aug. 13, 2009.

SAJA Pharmaceuticals Co.: "Vesicare 10 mg and 5 mg" Sep. 26, 2007 (Sep. 26, 2007). 1 page. Retrieved from the internet: URL:http://www.sajaonline.net/pdf/Vesicare%20leaflet.pdf.

Salagen.RTM. (pilocarpine HCl) product insert (.COPYRGT. 2003 MGI Pharma, 25 Inc.).

Salah, R.S. et al., "Pilocarpine for Anticholinergic Adverse Effects Asscoaited with Desipramine Treatement"; American Journal of Psychiatry, 153(4): (1996): pp. 579.

Serra, Denise B. et al., (2005) "QT and QTc Interval with Standard and Supratherapeutic Doses of Darifenacin, a Muscarinic M3 Selective Receptor Antagonist for the Treatment of Overactive Bladder"; Journal Clinical Pharmacology, 45:1038-1047.

Siami, Paul et al., "A Multicenter, Prospective, Open-Label Study of Tolterodine Extended-Release 4 mg for Overactive Bladder: The Speed of Onset of Therapeutic Assessment Trial (STAT)," Clinical Therapeutics, (2002) 24:616-628.

Smulders, Ronald A. et al., "Pharmacokinetics and Safety of Solinfenacin Succinate in Healthy Young Men," Journal of Clinical Pharmacology, (2004) 44:1023-1033.

St. Peter et al., "Pharmacokinetics of Pilocarpine in Subjects with Varying Degrees of Renal Function", J Clin Pharmacol, 40: 1470-1475, (2000).

Stedman's Medical Dictionary (published by Houghton Mifflin Company) (1995), p. 642.

Steers, William et al. (2005) "An Investigation of Dose Titration with Darifenacin, an Mx-Selective Receptor Antagonist"; BJU International 95:580-586.

Tiwari, Atul and Krishna S. Naruganahalli, "Current and Emerging Investigational Medical Therapies for the Treatment of Overactive Bladder," Expert Opin. Investig. Drugs, (2006) 15(9):1017-1037.

U.S. Department of Health and Human Services, Food and Drug Administration, Center for Drug Evaluation and Research (COER), "Guidance for Industry: Waiver of in Vivo Bioavailability and Bioequivalence Studies for Immediate-Release Solid Oral DosageForms Based on a Biopharmaceutics Classification System," Section II(C); Aug. 2000.

Versi, Eboo et al., "Dry Mouth with Conventional and Controlled-Releases Oxybutynin in Urinary Incontinence," Obstetrics & Gynecology, (2000) 95:718-721.

Extended European Search Report and Written Opinion issued in EP 11763548 dated Sep. 17, 2014.

Extended European Search Report and Written Opinion issued in EP 18212881.9 dated Mar. 26, 2019.

Search and Exam Report issued by the Austrian Patent Office in Singapore Patent Application No. 201003060-9 dated Jan. 3, 2012.

First Examination Report for Indian Patent Application No. 2078/MUMNP/2013 dated Nov. 11, 2018.

Prescribing information for VESICARE(TM), Jan. 2012.

Waldeck, Kristian et al., "Comparison of Oxybutynin and its Active Metabolite, N-Desethyl-Oxybutynin, in the Human Detrusor and Parotid Gland," The Journal of Urology, (1997) 157:1093-1097.

Wall et al. (2002) "Pharmacotherapy of Xerostomia in Primary Sjogren's Syndrome"; Pharmacotherapy, 22(5); pp. 621-629.

Watanabe, Kiyoshi, et al. (1986) "Oxybutynin hydrochloride: Effects of Oxybutynin hydrochloride on the Motilities of the Digestive Tracts and Urinary Bladder in Anesthetized Dogs"; Applied Pharmacology, vol. 31, No. 5; pp. 995-1106.

Yakushiji, T. et al., "Effects of Benzodiazepines and Non-Benzodiazepine Compounds on the GABA-induced Response in Frog Isolated Sensory Neurones", Br. J. Pharmacol. (1989), 98, 735-740.

Yoshida Akira et al. (2010) "The forefront for novel therapeutic agents based on the pathophysiology of lower urinary tract dysfunction: bladder selectivity based on in vivo drug-receptor binding characteristics of antimuscarinic agents fortreatment of overactive bladder"; Journal of Pharmacological Sciences, vol. 112. No. 2; pp. 142-150.

Zinner, Norman et al., "Trospium Chloride Improves Overative Bladder Symptoms: A Multicenter Phase III Trial," Journal of Urology, (2004) 171:2311-2315.

Mijnhout et al. "Oxybutynin: Dry Days for Patients with Hyperhydrosis." Netherlands: The Journal of Medicine. vol. 64, Van Zuiden Communications, Oct. 2006, pp. 326-29.

METHODS AND COMPOSITIONS FOR TREATING HYPERHIDROSIS

CROSS REFERENCE TO RELATED APPLICATIONS

This application is a continuation of U.S. application Ser. No. 15/456,414, filed Mar. 10, 2017, now U.S. Pat. No. 10,328,057 issued Jun. 25, 2019, which is a continuation of International Patent Application No. PCT/US2016/014150, filed Jan. 20, 2016, the entire disclosures of which are incorporated herein by reference.

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

INTRODUCTION

Sweat is an essential physiological function to human survival and serves as a body's coolant, protecting it from overheating. Eccrine glands secrete an odorless, clear fluid that helps the body to control its temperature by promoting heat loss through evaporation. Apocrine glands produce a thicker fluid which is often found in the armpits and near the genitals. Both the eccrine and apocrine sweat glands are activated by nerves.

Hyperhidrosis is a disorder characterized by an abnormal amount of sweating in excess of that required for regulation of body temperature. Hyperhidrosis can be either generalized or localized to specific parts of the body, including the hands, feet, armpits and genital region. It is estimated that 2-3% of Americans suffer from excessive sweating of the underarms (axillary hyperhidrosis), of the palms (palmar hyperhidrosis) or the soles of the feet (plantar hyperhidrosis). Prolonged hyperhidrosis can result in cold and clammy hands, dehydration as well as skin infections. However, most commonly subjects suffering from hyperhidrosis experience a significant quality of life burden from a psychological, emotional and social perspective, often modifying their lifestyles to accommodate the condition, which can lead to a disabling professional, academic and social life.

SUMMARY

Aspects of the disclosure include methods for treating hyperhidrosis in a subject with a composition including a muscarinic antagonist and a muscarinic agonist. In practicing methods according to certain embodiments, a therapeutically effective amount of a composition having a muscarinic antagonist, or a pharmaceutically acceptable salt thereof, and a muscarinic agonist, or a pharmaceutically acceptable salt thereof, is administered to a subject and is sufficient to reduce hyperhidrosis in the subject and to reduce a dry mouth side effect of the muscarinic antagonist. Compositions for practicing the subject methods are also described as well as dose units containing one or more of the subject compositions.

Certain muscarinic agonists, in particular pilocarpine, are known to cause an increase in sweating. See, e.g., Salagen® (pilocarpine HCl) product insert (©2003 MGI Pharma, Inc.). Accordingly, it was unexpected that the administration of a composition including both a muscarinic antagonist and a muscarinic agonist, such as pilocarpine, according to the subject methods, would effectively treat hyperhidrosis while reducing a dry mouth side effect of the muscarinic antagonist. Surprisingly, as demonstrated herein, it was found that the muscarinic agonist neither diminished the efficacy of the muscarinic antagonist in treating hyperhidrosis nor caused an increase in sweating in the subjects as is generally expected with the administration of a muscarinic agonist such as pilocarpine.

DETAILED DESCRIPTION

Figure 1:
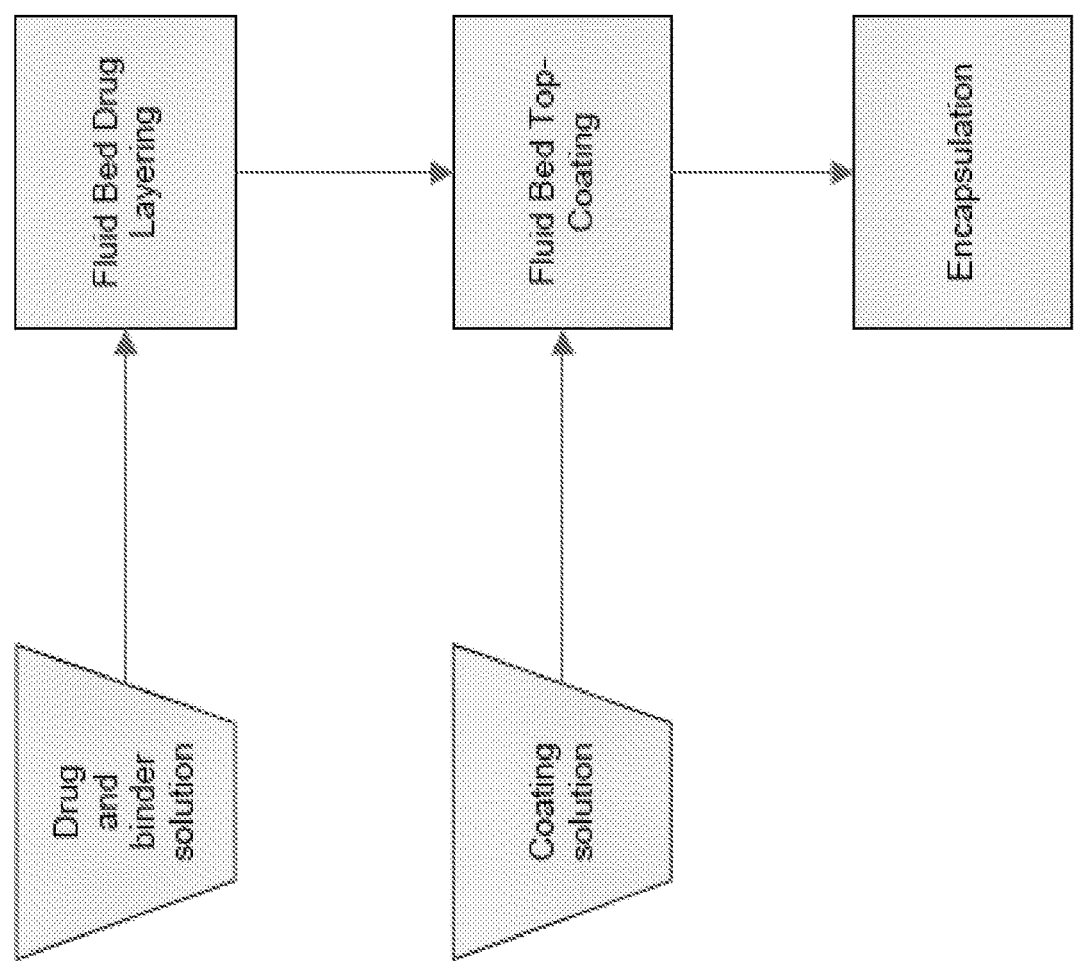
FIG. 1 illustrates a process for manufacturing pilocarpine beads according to one embodiment.

Aspects of the disclosure include methods and compositions for treating hyperhidrosis in a subject with a composition including a muscarinic antagonist and a muscarinic agonist. In practicing methods according to certain embodiments, a therapeutically effective amount of a composition having a muscarinic antagonist or a pharmaceutically acceptable salt thereof and a muscarinic agonist or a pharmaceutically acceptable salt thereof is administered to a subject and is sufficient to reduce hyperhidrosis in the subject and to reduce a dry mouth side effect of the muscarinic antagonist in the subject.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating non-recited number may be a number which, in the context in which it is presented, provides the substantial equivalent of the specifically recited number. In some embodiments, the term "about", when used to modify a value, encompasses a value that is within 15%, e.g., within 10%, e.g., within 5%, of the value modified by the term "about".

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any recited element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order which is logically possible.

In further describing various embodiments of the disclosure, methods for treating hyperhidrosis by administering a therapeutically effective amount of a composition including a muscarinic antagonist or a pharmaceutically acceptable salt thereof and a muscarinic agonist or a pharmaceutically acceptable salt thereof are reviewed first in greater detail. Next, compositions and dose units for practicing methods of the subject disclosure are described.

Methods for Treating Hyperhidrosis

As summarized above, aspects of the disclosure include methods for treating hyperhidrosis by administering to a subject a composition having a therapeutically effective amount of a composition including a muscarinic antagonist or a pharmaceutically acceptable salt thereof and a muscarinic agonist or a pharmaceutically acceptable salt thereof. In embodiments of the present disclosure, the subject methods may be employed in the treatment of primary (focal) hyperhidrosis or secondary hyperhidrosis. In some embodiments, the subject methods include treating localized hyperhidrosis, such as axillary hyperhidrosis, palmar hyperhidrosis, plantar hyperhidrosis, or craniofacial hyperhidrosis. In some embodiments, the subject methods include treating generalized hyperhidrosis or compensatory sweating post-surgery. By treatment is meant that at least an amelioration of the symptoms or characteristics associated with hyperhidrosis afflicting the subject is achieved, where amelioration is used in a broad sense to refer to at least a reduction in the magnitude, such as a reduction in excessive sweating experienced by the subject. As such, treatment also includes situations where the pathological condition, or at least symptoms or characteristics associated therewith, are completely inhibited, e.g., prevented from happening, or stopped, e.g., terminated, such that the subject no longer suffers from the condition, or at least the symptoms that characterize the condition. The phrase "treating hyperhidrosis" is used herein in its conventional sense to refer to reducing, ameliorating or altogether eliminating excessive sweating as experienced by the subject. In certain embodiments, treating hyperhidrosis includes reducing excessive sweating experienced by the subject, such as where excessive sweating by the subject is reduced by about 5% or more as reported by the subject or as determined by gravimetric assessments, on the Hyperhidrosis Disease Severity Scale (HDSS), by measurement by transdermal epidural water vapor loss (e.g., Vapometer, Delfin Technologies, Kuopio Finland), on the Hyperhidrosis Visual Quantification Scale (HHVQS, e.g., HHVQSa or HHVQSp), on the Hyperhidrosis Visual Analog Scale (HHVAS) or any combination thereof. For example, the subject methods may include treating hyperhidrosis, wherein the treatment is sufficient to reduce excessive sweating by 10% or more, such as by about 25% or more, such as by about 50% or more, such as by about 75% or more, such as by about 90% or more and including reducing excessive sweating experienced by the subject by about 99% or more as reported by the subject or as determined by gravimetric assessments, on the Hyperhidrosis Disease Severity Scale (HDSS), by measurement by transdermal epidural water vapor loss (e.g., Vapometer, Delfin Technologies, Kuopio Finland), on the Hyperhidrosis Visual Quantification Scale (HHVQS, e.g., HHVQSa or HHVQSp), on the Hyperhidrosis Visual Analog Scale (HHVAS) or any combination thereof. In other embodiments, treating hyperhidrosis includes altogether eliminating excessive sweating experienced by the subject.

In some embodiments, the treatment is sufficient to reduce excessive sweating by about 5% to about 25%, about 25% to about 50%, about 75% to about 90%, or by about 90% to about 99%, as reported by the subject or as determined by gravimetric assessments, on the Hyperhidrosis Disease Severity Scale (HDSS), by measurement by transdermal epidural water vapor loss (e.g., Vapometer, Delfin Technologies, Kuopio Finland), on the Hyperhidrosis Visual Quantification Scale (HHVQS, e.g., HHVQSa or HHVQSp), on the Hyperhidrosis Visual Analog Scale (HHVAS) or any combination thereof.

As described in greater detail below, the subject compositions include an amount of a muscarinic antagonist or a pharmaceutically acceptable salt thereof and an amount of a muscarinic agonist or a pharmaceutically acceptable salt thereof. According to certain aspects of the present disclosure, the muscarinic agonist is present in the composition in an amount sufficient to reduce one or more side effects caused by the muscarinic antagonist, such as dry mouth. In certain instances, the muscarinic antagonist is oxybutynin or a pharmaceutically acceptable salt thereof and the muscarinic agonist is pilocarpine or a pharmaceutically acceptable salt thereof and the pilocarpine or a pharmaceutically acceptable salt thereof is present in the composition in an amount sufficient to reduce one or more side effects caused by the administration of oxybutynin or a pharmaceutically acceptable salt thereof. In certain embodiments, pilocarpine or a pharmaceutically acceptable salt thereof is present in an amount sufficient to reduce dry mouth caused by oxybutynin or a pharmaceutically acceptable salt thereof. The muscarinic agonist or a pharmaceutically acceptable salt thereof (e.g., pilocarpine or pilocarpine HCl) may be administered with the muscarinic antagonist or a pharmaceutically acceptable salt thereof (e.g., oxybutynin or oxybutynin HCl) to the subject in an amount sufficient to alleviate dry mouth by about 25% or more, such as by about 50% or more, such as by about 75% or more, such as by about 90% or more, such as by about 95% or more and including by about 99% or more as reported by the subject or as assessed by the Dry Mouth Visual Analog Scale (DMVAS), by measuring salivary flow, by a Dry Mouth Severity/Incidence Questionnaire, e.g., as described herein, or a combination thereof.

In some embodiments, the muscarinic agonist or a pharmaceutically acceptable salt thereof (e.g., pilocarpine or pilocarpine HCl) may be administered with the muscarinic antagonist or a pharmaceutically acceptable salt thereof (e.g., oxybutynin or oxybutynin HCl) to the subject in an amount sufficient to reduce the severity of dry mouth by about 25% to about 50%, by about 50% to about 75%, by about 75% to about 90%, from about 90% to about 95%, or from about 95% to about 99% or more as reported by the subject or as assessed by the Dry Mouth Visual Analog Scale (DMVAS), by measuring salivary flow, by a Dry Mouth Severity/Incidence Questionnaire, e.g., as described herein, or a combination thereof.

In certain embodiments the muscarinic agonist or a pharmaceutically acceptable salt thereof (e.g., pilocarpine or pilocarpine HCl) is administered with the muscarinic antagonist or a pharmaceutically acceptable salt thereof (e.g., oxybutynin or oxybutynin HCl) to the subject in an amount sufficient to completely alleviate dry mouth caused by the muscarinic antagonist as reported by the subject or as assessed by the Dry Mouth Visual Analog Scale (DMVAS), by measuring salivary flow, by a Dry Mouth Severity/Incidence Questionnaire, e.g., as described herein, or a combination thereof.

In some embodiments, the muscarinic agonist or a pharmaceutically acceptable salt thereof (e.g., pilocarpine or pilocarpine HCl) may be administered with the muscarinic antagonist or a pharmaceutically acceptable salt thereof (e.g. oxybutynin or oxybutynin HCl) to the subject in an amount sufficient to reduce the number of incidences of moderate to severe dry mouth by about 25% to about 50%, by about 50% to about 75%, by about 75% to about 90%, from about 90% to about 95%, or from about 95% to about 99% or more as reported by the subject or as assessed by the Dry Mouth Visual Analog Scale (DMVAS), by measuring salivary flow, by a Dry Mouth Severity/Incidence Questionnaire, e.g., as described herein, or a combination thereof.

In certain embodiments the muscarinic agonist or a pharmaceutically acceptable salt thereof (e.g., pilocarpine or pilocarpine HCl) is administered with the muscarinic antagonist or a pharmaceutically acceptable salt thereof (e.g., oxybutynin or oxybutynin HCl) to the subject in an amount sufficient to completely eliminate the number of incidences of moderate or severe dry mouth caused by the muscarinic antagonist as reported by the subject or as assessed by the Dry Mouth Visual Analog Scale (DMVAS), by measuring salivary flow, by a Dry Mouth Severity/Incidence Questionnaire, e.g., as described herein, or a combination thereof.

Certain muscarinic agonists, in particular pilocarpine, are known to cause an increase in sweating, for example as shown in Jacobs: *A Multicenter Maintenance Study of Oral Pilocarpine Tablets for Radiation-Induced Xerostomia, Oncology*, 1996; 10 {Suppl}:16-20; and Cheshire and Fealey: *Drug-Induced Hyperhidrosis and Hypohidrosis Incidence, Prevention and Management, Drug Safety*, 2008; 31(2):109-126; and in the Salagen® (pilocarpine HCl) product insert (© 2003 MGI Pharma, Inc.). In view of such teachings, it was unexpectedly found that administering a muscarinic agonist in combination with a muscarinic antagonist to a subject did not result in an increase in sweating in the subjects and did not significantly diminish the efficacy of the muscarinic antagonist in the context of hyperhidrosis treatment. As described in greater detail in the experimental section below, when administering a composition including a muscarinic antagonist and a muscarinic agonist in accordance with the present disclosure, the composition is effective at treating hyperhidrosis by reducing excessive sweating experienced by the subject such as reported by the subject or as measured by gravimetric assessments, on the Hyperhidrosis Disease Severity Scale (HDSS), by measurement by transdermal epidural water vapor loss (e.g., Vapometer, Delfin Technologies, Kuopio Finland), on the Hyperhidrosis Visual Quantification Scale (HHVQS, e.g., HHVQSa or HHVQSp), on the Hyperhidrosis Visual Analog Scale (HHVAS) or any combination thereof.

In certain embodiments, administering a composition including a muscarinic antagonist or a pharmaceutically acceptable salt thereof and a muscarinic agonist or a pharmaceutically acceptable salt thereof in accordance with the present disclosure is at least as effective at treating hyperhidrosis by reducing excessive sweating by the subject as administering the muscarinic antagonist or a pharmaceutically acceptable salt thereof alone. By "at least as effective" in this context is meant that the composition containing a combination of muscarinic antagonist, or a pharmaceutically acceptable salt thereof, and a muscarinic agonist or a pharmaceutically acceptable salt thereof is at least 70% as effective at reducing hyperhidrosis in the subject as when the muscarinic antagonist or pharmaceutically acceptable salt thereof is administered alone, as reported by the subject or as measured by gravimetric assessments, on the Hyperhidrosis Disease Severity Scale (HDSS), by measurement by transdermal epidural water vapor loss (e.g., Vapometer, Delfin Technologies, Kuopio Finland), on the Hyperhidrosis Visual Quantification Scale (HHVQS, e.g., HHVQSa or HHVQSp), on the Hyperhidrosis Visual Analog Scale (HHVAS) or any combination thereof, such as at least 85%, such as at least 90%, such as at least 95%, such as at least 97% and including at least 99% as effective at reducing hyperhidrosis in the subject as when a muscarinic antagonist or a pharmaceutically acceptable salt is administered alone.

In certain embodiments, the subject compositions of the muscarinic antagonist or a pharmaceutically acceptable salt thereof and muscarinic agonist or a pharmaceutically acceptable salt thereof are equally effective at reducing excessive sweating experienced by the subject as administration of the muscarinic antagonist or a pharmaceutically acceptable salt thereof alone, as reported by the subject or as measured by gravimetric assessments, on the Hyperhidrosis Disease Severity Scale (HDSS), by measurement by transdermal epidural water vapor loss (e.g., Vapometer, Delfin Technologies, Kuopio Finland), on the Hyperhidrosis Visual Quantification Scale (HHVQS, e.g., HHVQSa or HHVQSp), on the Hyperhidrosis Visual Analog Scale (HHVAS) or any combination thereof.

In certain embodiments, administering a muscarinic agonist or pharmaceutically acceptable salt thereof in combination with a muscarinic antagonist or pharmaceutically acceptable salt thereof in accordance with the present disclosure does not substantially reduce the efficacy of the muscarinic antagonist or pharmaceutically acceptable salt thereof in treating hyperhidrosis relative to administration of the muscarinic antagonist or a pharmaceutically acceptable salt thereof alone. For example, in embodiments, the muscarinic agonist or pharmaceutically acceptable salt thereof reduces the efficacy of the muscarinic antagonist or pharmaceutically acceptable salt thereof in treating hyperhidrosis by 30% or less as measured by gravimetric assessments, on the Hyperhidrosis Disease Severity Scale (HDSS), by measurement by transdermal epidural water vapor loss (e.g., Vapometer, Delfin Technologies, Kuopio Finland), on the Hyperhidrosis Visual Quantification Scale (HHVQS, e.g., HHVQSa or HHVQSp), on the Hyperhidrosis Visual Analog Scale (HHVAS), such as by 25% or less, such as by 20% or less, such as by 15% or less, such as by 10% or less, such as by 5% or less, such as by 2% or less and including by 1% or less as measured by gravimetric assessments, on the Hyperhidrosis Disease Severity Scale (HDSS), by measurement by transdermal epidural water vapor loss (e.g., Vapometer, Delfin Technologies, Kuopio Finland), on the Hyperhidrosis Visual Quantification Scale (HHVQS, e.g., HHVQSa or HHVQSp), on the Hyperhidrosis Visual Analog Scale (HHVAS). In certain embodiments, the muscarinic agonist or pharmaceutically acceptable salt thereof does not reduce the efficacy of the muscarinic antagonist or pharmaceutically acceptable salt thereof in treating hyperhidrosis at all (i.e., by 0%) as measured by gravimetric assessments, on the Hyperhidrosis Disease Severity Scale (HDSS), by measurement by transdermal epidural water vapor loss (e.g., Vapometer, Delfin Technologies, Kuopio Finland), on the Hyperhidrosis Visual Quantification Scale (HHVQS, e.g., HHVQSa or HHVQSp), on the Hyperhidrosis Visual Analog Scale (HHVAS).

In embodiments of the present disclosure, methods for treating hyperhidrosis in a subject are provided. By "subject" is meant the person or organism administered the composition including a therapeutically effective amount of a composition including a muscarinic antagonist or a pharmaceutically acceptable salt thereof and a muscarinic agonist or a pharmaceutically acceptable salt thereof. As such, subjects of the disclosure may include but are not limited to mammals, e.g., humans and other primates, such as chimpanzees and other apes and monkey species; and the like, where in certain embodiments the subject are humans.

In embodiments of the present disclosure, methods include administering to a subject a therapeutically effective amount of a composition including a muscarinic antagonist or a pharmaceutically acceptable salt thereof and a muscarinic agonist or a pharmaceutically acceptable salt thereof. The muscarinic antagonist may be any type of anticholinergic agent that blocks the activity of the muscarinic acetylcholine receptor, such as blockers of the $M_1$, $M_2$, $M_3$, $M_4$ or $M_5$ muscarinic receptor isoforms. In some embodiments, muscarinic antagonists suitable for use in the subject methods is one or more of oxybutynin, tolterodine, 5-hydroxymethyl tolterodine, fesoterodine, solifenacin, darifenaccin, tropsium, imidafenacin, propiverine or dicyclomine or a pharmaceutically acceptable salt thereof. In certain embodiments, the muscarinic antagonist is oxybutynin (4-Diethylaminobut-2-ynyl 2-cyclohexyl-2-hydroxy-2-phenylethanoate) or a pharmaceutically acceptable salt thereof.

Depending on the physiology of the subject, the amount of muscarinic antagonist or pharmaceutically acceptable salt thereof administered to the subject may vary, such as 0.5 mg or more, such as 1.5 mg or more, such as 2.5 mg or more, such as 3.0 mg or more, such as 3.5 mg or more, such as 4.0 mg or more, such as 4.5 mg or more, such as 5.0 mg or more, such as 5.5 mg or more, such as 6.0 mg or more, such as 6.5 mg or more, such as 7.0 mg or more, such as 7.5 mg or more, such as 8.0 mg or more, such as 8.5 mg or more, such as 9.0 mg or more, such as 9.5 mg or more and including 10 mg or more. For example, the amount of muscarinic antagonist administered to the subject may range from 0.5 mg to 50 mg, such as from 1 mg to 40 mg, such as from 2 mg to 40 mg, such as from 3 mg to 30 mg, such as from 4 mg to 25 mg, such as from 5 mg to 20 mg and including from 5 mg to 10 mg, for example 7.5 mg. In certain embodiments, the amount of muscarinic antagonist or pharmaceutically acceptable salt thereof administered to the subject is 7.5 mg. In other embodiments, the amount of muscarinic antagonist or pharmaceutically acceptable salt thereof administered to the subject is 5.0 mg.

In certain embodiments, the muscarinic antagonist is oxybutynin or pharmaceutically acceptable salt thereof and the amount of oxybutynin or pharmaceutically acceptable salt thereof administered to the subject is 0.5 mg or more, such as 1.5 mg or more, such as 2.5 mg or more, such as 3.0 mg or more, such as 3.5 mg or more, such as 4.0 mg or more, such as 4.5 mg or more, such as 5.0 mg or more, such as 5.5 mg or more, such as 6.0 mg or more, such as 6.5 mg or more, such as 7.0 mg or more, such as 7.5 mg or more, such as 8.0 mg or more, such as 8.5 mg or more, such as 9.0 mg or more, such as 9.5 mg or more and including 10 mg or more. For example, the amount of oxybutynin or pharmaceutically acceptable salt thereof administered to the subject may range from 0.5 mg to 50 mg, such as from 1 mg to 45 mg, such as from 2 mg to 40 mg, such as from 3 mg to 30 mg, such as from 4 mg to 25 mg, such as from 5 mg to 20 mg and including from 5 mg to 10 mg, for example 7.5 mg. In certain embodiments, the amount of oxybutynin or pharmaceutically acceptable salt thereof administered to the subject is 7.5 mg. In other embodiments, the amount of oxybutynin or pharmaceutically acceptable salt thereof administered to the subject is 5.0 mg.

In embodiments of the present disclosure, the muscarinic agonist may be any type of agent that activates the activity of the muscarinic acetylcholine receptor, such as activators of the $M_1$, $M_2$, $M_3$, $M_4$ or $M_5$ muscarinic receptor isoforms. In some embodiments, muscarinic agonists suitable for use in the subject methods is one or more of pilocarpine, choline, acetylcholine, carbachol, methacholine, bethanechol, muscarine, nicotine, or oxotremorine. In certain embodiments, the muscarinic agonist is pilocarpine ((3S,4R)-3-Ethyl-4-

((1-methyl-1H-imidazol-5-yl)methyl)dihydrofuran-2(3H)-one) or a pharmaceutically acceptable salt thereof.

Depending on the physiology of the subject and the amount of muscarinic agonist administered, the amount of muscarinic agonist or pharmaceutically acceptable salt thereof administered to the subject may vary, such as 0.5 mg or more, such as 1.5 mg or more, such as 2.5 mg or more, such as 3.0 mg or more, such as 3.5 mg or more, such as 4.0 mg or more, such as 4.5 mg or more, such as 5.0 mg or more, such as 5.5 mg or more, such as 6.0 mg or more, such as 6.5 mg or more, such as 7.0 mg or more, such as 7.5 mg or more, such as 8.0 mg or more, such as 8.5 mg or more, such as 9.0 mg or more, such as 9.5 mg or more and including 10 mg or more. For example, the amount of muscarinic agonist administered to the subject may range from 0.5 mg to 50 mg, such as from 1 mg to 45 mg, such as from 2 mg to 40 mg, such as from 3 mg to 30 mg, such as from 4 mg to 25 mg, such as from 5 mg to 20 mg and including from 3 mg to 10 mg, for example 7.5 mg. In certain embodiments, the amount of muscarinic agonist or pharmaceutically acceptable salt thereof administered to the subject is 7.5 mg. In other embodiments, the amount of muscarinic agonist or pharmaceutically acceptable salt thereof administered to the subject is 5.0 mg.

In certain embodiments, the muscarinic agonist is pilocarpine or a pharmaceutically acceptable salt thereof and the amount of pilocarpine or pharmaceutically acceptable salt thereof administered to the subject is 0.5 mg or more, such as 1.5 mg or more, such as 2.5 mg or more, such as 3.0 mg or more, such as 3.5 mg or more, such as 4.0 mg or more, such as 4.5 mg or more, such as 5.0 mg or more, such as 5.5 mg or more, such as 6.0 mg or more, such as 6.5 mg or more, such as 7.0 mg or more, such as 7.5 mg or more, such as 8.0 mg or more, such as 8.5 mg or more, such as 9.0 mg or more, such as 9.5 mg or more and including 10 mg or more. For example, the amount of pilocarpine or pharmaceutically acceptable salt thereof administered to the subject may range from 0.5 mg to 50 mg, such as from 1 mg to 45 mg, such as from 2 mg to 40 mg, such as from 3 mg to 30 mg, such as from 4 mg to 25 mg, such as from 5 mg to 20 mg and including from 3 mg to 10 mg, for instance 7.5 mg. In certain embodiments, the amount of pilocarpine or pharmaceutically acceptable salt thereof administered to the subject is 7.5 mg. In other embodiments, the amount of pilocarpine or pharmaceutically acceptable salt thereof administered to the subject is 5.0 mg.

The mass ratio of the muscarinic antagonist or pharmaceutically acceptable salt thereof and the muscarinic agonist or pharmaceutically acceptable salt thereof administered to the subject may vary, ranging between 1:1 and 1:2.5; 1:2.5 and 1:5; 1:5 and 1:10; 1:10 and 1:25; 1:25 and 1:50; 1:50 and 1:100, or a range thereof. For example, where the muscarinic antagonist is oxybutynin or a pharmaceutically acceptable salt thereof and the muscarinic agonist is pilocarpine or a pharmaceutically acceptable salt thereof, the mass ratio of the oxybutynin and pilocarpine administered to the subject may range from 1:1 to 1:10; or from 1:5 to 1:25; or from 1:10 to 1:50; or from 1:25 to 1:100.

In some embodiments, the mass ratio of the muscarinic agonist or pharmaceutically acceptable salt thereof and the muscarinic antagonist or pharmaceutically acceptable salt thereof administered to the subject ranges between 1:1 and 1:2.5; 1:2.5 and 1:5; 1:5 and 1:10; 1:10 and 1:25; 1:25 and 1:50; 1:50 and 1:100, or a range thereof. For example, where the muscarinic antagonist is oxybutynin or a pharmaceutically acceptable salt thereof and the muscarinic agonist is pilocarpine or a pharmaceutically acceptable salt thereof, the mass ratio of the pilocarpine and oxybutynin administered to the subject may range from 1:1 to 1:10; or from 1:5 to 1:25; or from 1:10 to 1:50 or from 1:25 to 1:100.

Accordingly, the dosage of muscarinic antagonist or pharmaceutically acceptable salt thereof and muscarinic agonist or pharmaceutically acceptable salt thereof may vary, ranging from about 0.1 mg/kg to 25 mg/kg per day, such as from 0.1 mg/kg to 20 mg/kg per day, such as 0.1 mg/kg to 18 mg/kg per day, such as 0.1 mg/kg to 15 mg/kg per day, such as 0.1 mg/kg to 10 mg/kg per day, and including 0.1 mg/kg to 5 mg/kg per day. In other embodiments, the dosage may range from 0.1 to 6.5 mg/kg four times per day (QID), such as 0.1 to 5 mg/kg QID, such as 0.1 mg/kg to 4 mg/kg QID. In other embodiments, the oral dosage may range from 0.01 mg/kg to 8.5 mg/kg three times per day (TID), such as 0.1 mg/kg to 6 mg/kg TID, such as 0.1 mg/kg to 5 mg/kg TID, and including as 0.1 mg/kg to 4 mg/kg TID. In yet other embodiments, the oral dosage may range from 0.1 mg/kg to 13 mg/kg two times per day (BID), such as 0.1 mg/kg to 12 mg/kg BID, such as 5 mg/kg to 10 mg/kg BID, including 0.1 mg/kg to 8 mg/kg BID.

In embodiments, the total daily amount of muscarinic antagonist or pharmaceutically acceptable salt thereof administered to the subject is 2.5 mg or more, such as 5 mg or more, such as 7.5 mg or more, such as 10 mg or more, such as 15 mg or more, such as 20 mg or more, such as 25 mg or more and including 30 mg or more. For example, the total daily amount of muscarinic antagonist administered to the subject may range from 0.5 mg to 50 mg, such as from 1 mg to 40 mg, such as from 2 mg to 40 mg, such as from 3 mg to 30 mg, such as from 4 mg to 25 mg, such as from 5 mg to 20 mg and including from 5 mg to 10 mg. In certain instances, the muscarinic antagonist is oxybutynin or a pharmaceutically acceptable salt thereof and the total daily amount of oxybutynin or pharmaceutically acceptable salt thereof administered to the subject is 2.5 mg or more, such as 5 mg or more, such as 7.5 mg or more, such as 10 mg or more, such as 15 mg or more, such as 20 mg or more, such as 25 mg or more and including 30 mg or more, such as ranging from 0.5 mg to 50 mg, such as from 1 mg to 40 mg, such as from 2 mg to 40 mg, such as from 3 mg to 30 mg, such as from 4 mg to 25 mg, such as from 5 mg to 20 mg and including from 5 mg to 10 mg.

In embodiments, the total daily amount of muscarinic agonist or pharmaceutically acceptable salt thereof administered to the subject is 2.5 mg or more, such as 5 mg or more, such as 7.5 mg or more, such as 10 mg or more, such as 15 mg or more, such as 20 mg or more, such as 25 mg or more and including 30 mg or more. For example, the total daily amount of muscarinic agonist administered to the subject may range from 0.5 mg to 50 mg, such as from 1 mg to 40 mg, such as from 2 mg to 40 mg, such as from 3 mg to 30 mg, such as from 4 mg to 25 mg, such as from 5 mg to 20 mg and including from 5 mg to 10 mg. In certain instances, the muscarinic agonist is pilocarpine or a pharmaceutically acceptable salt thereof and the total daily amount of pilocarpine or pharmaceutically acceptable salt thereof administered to the subject is 2.5 mg or more, such as 5 mg or more, such as 7.5 mg or more, such as 10 mg or more, such as 15 mg or more, such as 20 mg or more, such as 25 mg or more and including 30 mg or more, such as ranging from 0.5 mg to 50 mg, such as from 1 mg to 40 mg, such as from 2 mg to 40 mg, such as from 3 mg to 30 mg, such as from 4 mg to 25 mg, such as from 5 mg to 20 mg and including from 5 mg to 10 mg.

The amount of compound administered will depend on the physiology of the subject, the absorptivity of the muscarinic antagonist and muscarinic agonist by the subject, as well as the magnitude of therapeutic effect desired. Dosing schedules may include, but are not limited to administration five times per day, four times per day, three times per day, twice per day, once per day, three times per week, twice per week, once per week, twice per month, once per month, and any combination thereof.

In practicing the subject methods, compositions including a muscarinic antagonist or a pharmaceutically acceptable salt thereof (e.g., oxybutynin or a pharmaceutically acceptable salt thereof) and a muscarinic agonist or a pharmaceutically acceptable salt thereof (e.g., pilocarpine or a pharmaceutically acceptable salt thereof) may be administered to treat the subject for hyperhidrosis for a duration that varies, depending on the type of hyperhidrosis (e.g., generalized, palmar, plantar, axillary, craniofacial, compensatory sweating post-surgery, etc.) and severity of the condition, as determined by a qualified health care professional. For example, the subject compositions may be administered to treat hyperhidrosis for a period of 1 week or longer, such as 3 weeks or longer, such as 1 month or longer, such as 3 months or longer, such as 6 months or longer, such as 9 months or longer, such as 1 year or longer and including 5 years or longer.

In certain embodiments, compositions of the disclosure can be orally administered prior to, concurrent with, or subsequent to other agents for treating related or unrelated conditions. If provided at the same time as other agents, compositions of the invention can be provided in the same or in a different composition. For example, concurrent therapy may be achieved by administering compositions of the disclosure and a pharmaceutical composition including at least one other agent, such as an analgesic, which in combination comprise a therapeutically effective dose, according to a particular oral dosing regimen. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

Compositions including a muscarinic antagonist or a pharmaceutically acceptable salt thereof and muscarinic agonist or a pharmaceutically acceptable salt thereof may be administered to the subject by any convenient protocol as desired or appropriate for the subject, for example as a tablet, capsule, thin film, powder, suspension, solution, syrup, dispersion or emulsion. As described in greater detail below, the subject compositions may contain components conventional in pharmaceutical preparations, e.g. one or more carriers, binders, lubricants, excipients (e.g., to impart controlled release characteristics), pH modifiers, sweeteners, bulking agents, coloring agents or further active agents. In certain embodiments, compositions including the muscarinic antagonist or a pharmaceutically acceptable salt thereof and muscarinic agonist or a pharmaceutically acceptable salt thereof are capsules including immediate release beads including the muscarinic antagonist or a pharmaceutically acceptable salt thereof and delayed-immediate release beads including the muscarinic agonist or a pharmaceutically acceptable salt thereof. For example, subjects may be orally administered a capsule containing immediate release oxybutynin or a pharmaceutically acceptable salt thereof and delayed-immediate release pilocarpine or a pharmaceutically acceptable salt thereof.

In embodiments, subjects treated by the present methods exhibit a positive therapeutic response. By "positive therapeutic response" is meant that the subject exhibits a reduction or elimination of hyperhidrosis. For example, a subject exhibiting a positive therapeutic response to methods provided by the disclosure may exhibit responses including but not limited to a reduction or elimination of axillary, palmar, plantar, craniofacial hyperhidrosis, generalized hyperhidrosis, compensatory sweating post-surgery, as reported by the subject, or as determined by gravimetric assessments, on the Hyperhidrosis Disease Severity Scale (HDSS), by measurement by transdermal epidural water vapor loss (e.g., Vapometer, Delfin Technologies, Kuopio Finland), on the Hyperhidrosis Visual Quantification Scale (HHVQS, e.g., HHVQSa or HHVQSp), on the Hyperhidrosis Visual Analog Scale (HHVAS) or any combination thereof.

Treatment regimens may include administering a single dose unit or administering multiple dose units. In certain embodiments, treatment regimens include administering multiple dose units. Unless specifically stated otherwise, "dose unit" as used herein refers to a premeasured amount of a composition that contains a muscarinic antagonist or pharmaceutically acceptable salt thereof (e.g., oxybutynin or oxybutynin HCl) and a muscarinic agonist or pharmaceutically acceptable salt thereof (e.g., pilocarpine or pilocarpine HCl). A "single dose unit" is a single unit of a combination of a muscarinic antagonist or pharmaceutically acceptable salt thereof and a muscarinic agonist or pharmaceutically acceptable salt thereof, where the single dose unit provides a therapeutically effective amount of the composition. "Multiple dose units" or "multiples of a dose unit" or a "multiple of a dose unit" refers to at least two single dose units.

As referred to herein, a dosage interval is a single administration (e.g., orally, injection, intravenously, etc.) of a therapeutically effective amount of the composition including a muscarinic antagonist or a pharmaceutically acceptable salt thereof and a muscarinic agonist or a pharmaceutically acceptable salt thereof. By "multiple dosage intervals" is meant more than one dosage of the composition including the muscarinic antagonist or a pharmaceutically acceptable salt thereof and the muscarinic agonist or a pharmaceutically acceptable salt thereof is administered to the subject in a sequential manner. As such, the first dosage is either removed or completely consumed by the subject and the second dosage is administered to the subject. In practicing methods of the disclosure, treatment regimens may include two or more dosing intervals, such as three or more dosing intervals, such as four or more dosing intervals, such as five or more dosing intervals, including ten or more dosing intervals. In some embodiments, the disclosed methods include treating chronic hyperhidrosis by administering multiple doses over an extended period. Alternatively or in addition, methods and compositions of the disclosure may be administered to treat an acute condition (e.g., hyperhidrosis caused by another drug, etc.) in single or multiple doses for a relatively short period, for example one to two weeks.

The duration between dosage intervals in a multiple dosage interval treatment regimen may vary, depending on the physiology of the subject or by the treatment regimen as determined by a health care professional. In certain instances, the duration between dosage intervals in a multiple dosage treatment regimen may be predetermined and follow at regular intervals. As such, the time between dosing intervals may vary and may be 0.5 hours or longer, such as 1 hour or longer, such as 2 hours or longer, such as 4 hours or longer, such as 8 hours or longer, such as 12 hours or longer, such as 16 hours or longer, such as 24 hours or longer, such as 48 hours or longer and including 72 hours or longer.

In other instances, the duration between dosage intervals may depend on the response of the subject to one or more previous dosage intervals (e.g., amount of reduction in excessive sweating) as determined by a health care professional during the time between dosage intervals. For example, a subsequent dosage interval may commence if excessive sweating does not decrease as desired in response to a dosage interval or increases between dosage intervals. In yet other instances, the duration between dosage intervals may depend on the reduction of excessive sweating reported by the subject or as determined by gravimetric assessments, on the Hyperhidrosis Disease Severity Scale (HDSS), by measurement by transdermal epidural water vapor loss (e.g., Vapometer, Delfin Technologies, Kuopio Finland), on the Hyperhidrosis Visual Quantification Scale (HHVQS, e.g., HHVQSa or HHVQSp), on the Hyperhidrosis Visual Analog Scale (HHVAS) or any combination thereof.

In some embodiments, methods include dosage intervals spanning multiple days. By "multiple day dosing" is meant that the muscarinic antagonist or pharmaceutically acceptable salt thereof and muscarinic agonist or pharmaceutically acceptable salt thereof are administered to the subject over a period of time that is longer than 1 day, such as 2 days or longer, such as 3 days or longer, such as 5 days or longer, such as 7 days or longer, including 10 days or longer.

In certain embodiments, the amount of muscarinic antagonist or a pharmaceutically acceptable salt thereof and muscarinic agonist or a pharmaceutically acceptable salt thereof administered to the subject is sufficient to achieve a particular pharmacokinetic profile. As used herein, a "PK profile" refers to a profile of drug concentration in blood or plasma. Such a profile can be a relationship of drug concentration over time (i.e., a "concentration-time PK profile") or a relationship of drug concentration versus number of doses administered (i.e., a "concentration-dose PK profile".) A PK profile is characterized by PK parameters. As used herein, a "PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

For purposes of describing the features of dose units of the present disclosure, "PK parameter values" that define a PK profile include drug Cmax (e.g., muscarinic antagonist or muscarinic agonist Cmax), total drug exposure (e.g., area under the curve) (e.g., muscarinic antagonist of muscarinic agonist exposure) and 1/(drug Tmax) (such that a decreased 1/Tmax is indicative of a delay in Tmax relative to a reference Tmax) (e.g., 1/muscarinic antagonist or 1/muscarinic agonist Tmax). Thus a decrease in a PK parameter value relative to a reference PK parameter value can indicate, for example, a decrease in drug Cmax, a decrease in drug exposure, and/or a delayed Tmax.

In some embodiments, methods include administering a composition containing a muscarinic antagonist or a pharmaceutically acceptable salt thereof and a muscarinic agonist or a pharmaceutically acceptable salt thereof such that peak plasma concentration of muscarinic antagonist or a pharmaceutically acceptable salt thereof and the muscarinic agonist or a pharmaceutically acceptable salt thereof are achieved at about the same time. In other words, the composition (as described in greater detail below) is formulated such that maximum concentration of muscarinic agonist or a pharmaceutically acceptable salt thereof is achieved in the plasma at the same time as the maximum concentration of muscarinic antagonist or a pharmaceutically acceptable salt thereof.

In certain embodiments, dose units of the present disclosure can be adapted to provide for a modified PK profile for either the muscarinic antagonist or a pharmaceutically acceptable salt thereof or muscarinic agonist or a pharmaceutically acceptable salt thereof, e.g., a PK profile that is different from that achieved from dosing a given muscarinic antagonist or a pharmaceutically acceptable salt thereof or muscarinic agonist or a pharmaceutically acceptable salt thereof alone. For example, dose units can provide for at least one of decreased drug Cmax, delayed drug Tmax and/or decreased drug exposure compared to ingestion of a dose of the muscarinic antagonist or muscarinic agonist alone. Such a modification is due to the combination of muscarinic antagonist and muscarinic agonist in the dose unit.

In embodiments, a dose unit can be adapted to provide for a desired PK profile (e.g., a concentration-time PK profile) following ingestion of a single dose. A dose unit can be adapted to provide for a desired PK profile (e.g., a concentration-dose PK profile) following ingestion of multiple dose units (e.g., at least 2, at least 3, at least 4 or more dose units).

In certain embodiments, the combination of muscarinic antagonist or a pharmaceutically acceptable salt thereof and muscarinic agonist or a pharmaceutically acceptable salt thereof in a dose unit can provide a desired (or "pre-selected") PK profile (e.g., a concentration-time PK profile) following ingestion of a single dose. The PK profile of such a dose unit can be characterized by one or more of a pre-selected drug Cmax, a pre-selected drug Tmax or a pre-selected drug exposure. The PK profile of the dose unit can be modified compared to a PK profile achieved from the equivalent dosage of muscarinic antagonist or muscarinic agonist alone.

Combinations of relative amounts of muscarinic antagonist or a pharmaceutically acceptable salt thereof and muscarinic agonist or a pharmaceutically acceptable salt thereof that provide for a desired PK profile can be identified by dosing with a fixed amount of muscarinic antagonist or a pharmaceutically acceptable salt thereof and increasing amounts of muscarinic agonist or a pharmaceutically acceptable salt thereof, or with a fixed amount of muscarinic agonist or a pharmaceutically acceptable salt thereof and increasing amounts of muscarinic antagonist or a pharmaceutically acceptable salt thereof. One or more PK parameters can then be assessed, e.g., drug Cmax, drug Tmax, and drug exposure. Relative amounts of muscarinic antagonist or a pharmaceutically acceptable salt thereof and muscarinic agonist or a pharmaceutically acceptable salt thereof that provide for a desired PK profile are identified as amounts of muscarinic antagonist or a pharmaceutically acceptable salt thereof and muscarinic agonist or a pharmaceutically acceptable salt thereof for use in a dose unit. Assays can be conducted with different relative amounts of muscarinic antagonist or a pharmaceutically acceptable salt thereof and muscarinic agonist or a pharmaceutically acceptable salt thereof.

In vivo assays can be used to identify combinations of muscarinic antagonist or a pharmaceutically acceptable salt thereof and muscarinic agonist or a pharmaceutically acceptable salt thereof that provide for dose units that provide for a desired concentration-dose PK profile following ingestion of multiples of the dose unit (e.g., at least 2, at least 3, at least 4 or more). Ex vivo assays can be conducted by direct administration of muscarinic antagonist or a pharmaceutically acceptable salt thereof and muscarinic agonist or a pharmaceutically acceptable salt thereof into a tissue and/or its contents of an animal, such as the intestine, including by introduction by injection into the lumen of a ligated intestine (e.g., a gut loop, or intestinal loop, assay, or an inverted gut assay). An ex vivo assay can also be conducted by excising a tissue and/or its contents from an animal and introducing muscarinic antagonist or a pharmaceutically acceptable salt thereof and muscarinic agonist or a pharmaceutically acceptable salt thereof into such tissues and/or contents.

For example, a premeasured amount of muscarinic antagonist or a pharmaceutically acceptable salt thereof that is desired for a single dose unit is selected (e.g., an amount that provides an efficacious plasma drug level). A multiple of single dose units for which a relationship between that multiple and a PK parameter to be tested is then selected. For example, if a concentration-dose PK profile is to be designed for ingestion of 2, 3, 4, 5, 6, 7, 8, 9 or 10 dose units, then the amount of muscarinic antagonist or a pharmaceutically acceptable salt thereof equivalent to ingestion of that same number of dose units is determined (referred to as the "high dose"). The multiple of dose units can be selected based on the number of ingested pills at which drug Cmax is modified relative to ingestion of the single dose unit. Assays can be used to identify suitable combination(s) of muscarinic antagonist or a pharmaceutically acceptable salt thereof and muscarinic agonist or a pharmaceutically acceptable salt thereof to obtain a single dose unit that is therapeutically effective.

Compositions for Treating Hyperhidrosis Containing a Muscarinic Antagonist and a Muscarinic Agonist or Pharmaceutically Acceptable Salts Thereof As summarized above, aspects of the disclosure also include compositions containing a muscarinic antagonist or a pharmaceutically acceptable salt thereof and a muscarinic agonist or a pharmaceutically acceptable salt thereof suitable for practicing the methods described above. Compositions of interest take on any suitable form as desired or appropriate for administering to a subject in need of treatment for hyperhidrosis and may be in the form of a tablet, capsule, thin film, powder, suspension, solution, syrup, dispersion or emulsion. The composition can also contain components conventional in pharmaceutical preparations, e.g. one or more carriers, binders, lubricants, excipients (e.g., to impart controlled release characteristics), pH modifiers, sweeteners, bulking agents, coloring agents or further active agents. As described herein, a "pharmaceutical composition" refers to the combination of a muscarinic antagonist or a pharmaceutically acceptable salt thereof and a muscarinic agonist or a pharmaceutically acceptable salt thereof and a pharmaceutically acceptable excipient, with which each of the muscarinic antagonist or a pharmaceutically acceptable salt thereof and muscarinic agonist or a pharmaceutically acceptable salt thereof are administered to a subject.

As summarized above, the subject compositions include a muscarinic antagonist or a pharmaceutically acceptable salt thereof and a muscarinic agonist or a pharmaceutically acceptable salt thereof. "Pharmaceutically acceptable salt" refers to a salt of a compound, which possesses the desired pharmacological activity of the compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

In certain embodiments, compositions of the invention may also include an antimicrobial agent for preventing or deterring microbial growth, such as for example benzalkonium chloride, benzethonium chloride, benzyl alcohol, cetylpyridinium chloride, chlorobutanol, phenol, phenylethyl alcohol, phenylmercuric nitrate, thimersol, and any combinations thereof.

One or more antioxidants may also be employed. Antioxidants, which can reduce or prevent oxidation and thus deterioration of the composition, may include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and any combinations thereof.

One or more surfactants may also be included in compositions of the invention. For example, suitable surfactants may include, but are not limited to polysorbates, such as "Tween 20" and "Tween 80," and pluronics such as F68 and F88 (BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other cations.

Acids or bases may also be present in compositions of the invention. For example, acids may include but are not limited to hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and any combinations thereof. Examples of bases include, but are not limited to sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and any combinations thereof.

The amount of any individual excipient in the oral dosage composition will vary depending on the nature and function of the excipient, oral dosage delivery vehicle and particular needs of the composition. In some instances, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the oral dosage composition in an amount of about 1% to about 99% by weight, such as from about 5% to about 98% by weight, such as from about 15 to about 95% by weight of the excipient, including less than 30% by weight. Pharmaceutical excipients along with other excipients that may be employed in compositions of interest are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000, the disclosure of which is herein incorporated by reference.

Where the subject compositions are oral formulations, the pharmaceutical composition may include appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Compositions include a muscarinic antagonist or a pharmaceutically acceptable salt thereof. The muscarinic antagonist may be any type of anticholinergic agent that blocks the activity of the muscarinic acetylcholine receptor, such as blockers of the $M_1$, $M_2$, $M_3$, $M_4$ or $M_5$ muscarinic receptor isoforms. In some embodiments, the muscarinic antagonist is one or more of oxybutynin, tolterodine, 5-hydroxymethyl tolterodine, fesoterodine, solifenacin, darifenaccin, tropsium, imidafenacin, propiverine or dicyclomine or a pharmaceutically acceptable salt thereof. In certain embodiments, the muscarinic antagonist is oxybutynin (4-Diethylaminobut-2-ynyl 2-cyclohexyl-2-hydroxy-2-phenylethanoate) or a pharmaceutically acceptable salt thereof.

The amount of muscarinic antagonist or pharmaceutically acceptable salt thereof in the subject compositions may vary, such as 0.5 mg or more, such as 1.5 mg or more, such as 2.5 mg or more, such as 3.0 mg or more, such as 3.5 mg or more, such as 4.0 mg or more, such as 4.5 mg or more, such as 5.0 mg or more, such as 5.5 mg or more, such as 6.0 mg or more, such as 6.5 mg or more, such as 7.0 mg or more, such as 7.5 mg or more, such as 8.0 mg or more, such as 8.5 mg or more, such as 9.0 mg or more, such as 9.5 mg or more and including 10 mg or more. For example, the amount of muscarinic antagonist in compositions of interest may range from 0.5 mg to 25 mg, such as from 1 mg to 20 mg, such as from 2 mg to 15 mg and including from 3 mg to 10 mg, for example 7.5 mg. In certain embodiments, the muscarinic antagonist is oxybutynin or a pharmaceutically acceptable salt thereof and compositions of interest include 0.5 mg or more of oxybutynin or pharmaceutically acceptable salt thereof, such as 1.5 mg or more, such as 2.5 mg or more, such as 3.0 mg or more, such as 3.5 mg or more, such as 4.0 mg or more, such as 4.5 mg or more, such as 5.0 mg or more, such as 5.5 mg or more, such as 6.0 mg or more, such as 6.5 mg or more, such as 7.0 mg or more, such as 7.5 mg or more, such as 8.0 mg or more, such as 8.5 mg or more, such as 9.0 mg or more, such as 9.5 mg or more and including 10 mg or more of oxybutynin or pharmaceutically acceptable salt thereof. For example, compositions of interest may include from 0.5 mg to 25 mg of oxybutynin or pharmaceutically acceptable salt thereof, such as from 1 mg to 20 mg, such as from 2 mg to 15 mg and including from 3 mg to 10 mg, for instance 7.5 mg of oxybutynin or pharmaceutically acceptable salt thereof.

Compositions also include a muscarinic agonist or a pharmaceutically acceptable salt thereof. The muscarinic agonist may be any type of agent that activates the activity of the muscarinic acetylcholine receptor, such as activators of the $M_1$, $M_2$, $M_3$, $M_4$ or $M_5$ muscarinic receptor isoforms. In some embodiments, muscarinic agonists is one or more of pilocarpine, choline, acetylcholine, carbachol, methacholine, bethanechol, muscarine, nicotine, or oxotremorine. In certain embodiments, the muscarinic agonist is pilocarpine ((3S,4R)-3-Ethyl-4-((1-methyl-1H-imidazol-5-yl)methyl) dihydrofuran-2(3H)-one).

The amount of muscarinic agonist or pharmaceutically acceptable salt in the subject compositions may vary, such as 0.5 mg or more, such as 1.5 mg or more, such as 2.5 mg or more, such as 3.0 mg or more, such as 3.5 mg or more, such as 4.0 mg or more, such as 4.5 mg or more, such as 5.0 mg or more, such as 5.5 mg or more, such as 6.0 mg or more, such as 6.5 mg or more, such as 7.0 mg or more, such as 7.5 mg or more, such as 8.0 mg or more, such as 8.5 mg or more, such as 9.0 mg or more, such as 9.5 mg or more and including 10 mg or more. For example, the amount of muscarinic agonist in compositions of interest may range from 0.5 mg to 25 mg, such as from 1 mg to 20 mg, such as from 2 mg to 15 mg and including from 3 mg to 10 mg, for example 7.5 mg. In certain embodiments, the muscarinic agonist is pilocarpine or pharmaceutically acceptable salt thereof and compositions of interest include 0.5 mg or more of pilocarpine or pharmaceutically acceptable salt thereof, such as 1.5 mg or more, such as 2.5 mg or more, such as 3.0 mg or more, such as 3.5 mg or more, such as 4.0 mg or more, such as 4.5 mg or more, such as 5.0 mg or more, such as 5.5 mg or more, such as 6.0 mg or more, such as 6.5 mg or more, such as 7.0 mg or more, such as 7.5 mg or more, such as 8.0 mg or more, such as 8.5 mg or more, such as 9.0 mg or more, such as 9.5 mg or more and including 10 mg or more of pilocarpine or pharmaceutically acceptable salt thereof. For example, compositions of interest may include from 0.5 mg to 25 mg of pilocarpine or pharmaceutically acceptable salt thereof, such as from 1 mg to 20 mg, such as from 2 mg to 15 mg and including from 3 mg to 10 mg, for instance 7.5 mg of pilocarpine or pharmaceutically acceptable salt thereof.

The ratio of muscarinic antagonist or a pharmaceutically acceptable salt thereof and muscarinic agonist or a pharmaceutically acceptable salt thereof in the subject compositions may vary, ranging between 1:1 and 1:2.5; 1:2.5 and 1:5; 1:5 and 1:10; 1:10 and 1:25; 1:25 and 1:50; 1:50 and 1:100, or a range thereof. For example, where the muscarinic antagonist is oxybutynin or a pharmaceutically acceptable salt thereof and the muscarinic agonist is pilocarpine or a pharmaceutically acceptable salt thereof, the mass ratio of the oxybutynin or a pharmaceutically acceptable salt thereof and pilocarpine or a pharmaceutically acceptable salt thereof may range from 1:1 to 1:10; or from 1:5 to 1:25; or from 1:10 to 1:50; or from 1:25 to 1:100. In some embodiments, the mass ratio of the muscarinic agonist or pharmaceutically acceptable salt thereof and the muscarinic antagonist or pharmaceutically acceptable salt thereof ranges between 1:1 and 1:2.5; 1:2.5 and 1:5; 1:5 and 1:10; 1:10 and 1:25; 1:25 and 1:50; 1:50 and 1:100, or a range thereof. For example, where the muscarinic agonist is pilocarpine or a pharmaceutically acceptable salt thereof and the muscarinic antagonist is oxybutynin or a pharmaceutically acceptable salt thereof, the mass ratio of the pilocarpine or a pharmaceutically acceptable salt thereof and oxybutynin or a pharmaceutically acceptable salt thereof may range from 1:1 to 1:10; or from 1:5 to 1:25; or from 1:10 to 1:50 or from 1:25 to 1:100.

In certain embodiments, the compositions of interest are formulated as dose units, where the dosage of each of the muscarinic antagonist or a pharmaceutically acceptable salt thereof and muscarinic agonist or a pharmaceutically acceptable salt thereof in the dose unit ranges from about 0.1 mg/kg to 25 mg/kg, such as from 0.1 mg/kg to 20 mg/kg, such as 0.1 mg/kg to 18 mg/kg, such as 0.1 mg/kg to 15 mg/kg, such as 0.1 mg/kg to 10 mg/kg, and including 0.1 mg/kg to 5 mg/kg. In other embodiments, the subject compositions are formulated so that each of the muscarinic antagonist or a pharmaceutically acceptable salt thereof and muscarinic agonist or a pharmaceutically acceptable salt thereof can be administered in a dosage of from 0.1 to 6.5 mg/kg four times per day (QID), such as 0.1 to 5 mg/kg QID, such as 0.1 mg/kg to 4 mg/kg QID. In other embodiments, the subject compositions are formulated so that each of the muscarinic antagonist or a pharmaceutically acceptable salt thereof and muscarinic agonist or a pharmaceutically acceptable salt thereof can be administered in a dosage of from 0.01 mg/kg to 8.5 mg/kg three times per day (TID), such as 0.1 mg/kg to 6 mg/kg TID, such as 0.1 mg/kg to 5 mg/kg TID, and including as 0.1 mg/kg to 4 mg/kg TID. In yet other embodiments the subject compositions are formulated so that each of the muscarinic antagonist and muscarinic agonist can be administered in a dosage of from 0.1 mg/kg to 13 mg/kg two times per day (BID), such as 0.1 mg/kg to 12 mg/kg BID, such as 5 mg/kg to 10 mg/kg BID, including 0.1 mg/kg to 8 mg/kg BID.

In certain embodiments, compositions of interest are formulated to include an immediate release muscarinic antagonist or pharmaceutically acceptable salt thereof and a delayed onset immediate release muscarinic agonist or a pharmaceutically acceptable salt thereof. For example, the subject compositions may include an immediate release oxybutynin or a pharmaceutically acceptable salt thereof and a delayed-immediate release pilocarpine or a pharmaceutically acceptable salt thereof. The terms immediate release and delayed onset immediate release are used herein in their conventional sense to refer to the timing that the muscarinic antagonist or a pharmaceutically acceptable salt thereof and muscarinic agonist or a pharmaceutically acceptable salt thereof, respectively, are released after administration.

In some embodiments, the immediate release muscarinic antagonist or a pharmaceutically acceptable salt thereof (e.g., oxybutynin or oxybutynin HCl) is formulated to release 50% or more of the muscarinic antagonist or a pharmaceutically acceptable salt thereof within 10 minutes or less of administration of the composition to the subject, such as 60% or more, such as 75% or more, such as 90% or more, such as 95% or more and including 99% or more within 10 minutes or less of administration of the composition to the subject. In certain instances, the immediate release muscarinic antagonist or a pharmaceutically acceptable salt thereof (e.g., oxybutynin or oxybutynin HCl) is formulated to release 50% or more of the muscarinic antagonist or a pharmaceutically acceptable salt thereof immediately after administration of the composition to the subject, such as 60% or more, such as 75% or more, such as 90% or more, such as 95% or more and including 99% or more immediately after administration of the composition to the subject.

In embodiments, the immediate release muscarinic antagonist may be formulated as a powder, microparticle or as a granulate. The muscarinic antagonist may include a polymer, such as cellulose, microcrystalline cellulose, hydroxyethylcellulose, hydroxypropylcellulose, hydroxypropylmethylcellulose, carboxymethylcellulose, maltodextrin, sucrose, modified starch, a salt of alginic acid, soluble gums, carrageenan, polyvinylpyrrolidone (PVP) or polyvinylpolypyrrolidone (PVPP), ethylcellulose, cellulose acetate phthalate, hydroxypropylmethylcellulose phthalate, insoluble gums, polymethacrylate, a polyvinyl alcohol, shellac, and polyvinyl acetate phthalate or a combination thereof. In certain embodiments, the muscarinic antagonist component is a granulate of oxybutynin or a pharmaceutically acceptable salt thereof that includes microcrystalline cellulose and polyvinylpyrrolidone.

In other embodiments, the muscarinic antagonist component may further include a lipid excipient, such as glyceryl behenate, glycerol esters of fatty acids, glyceryl dibehenate, behenoyl macrogoglycerides, glyceryl distearate, glycerol distearate, glyceryl palmitostearate, lauroyl macrogoglycerides, stearoyl macrogoglycerides, abitec products, glyceryl mono-oleate, medium chain mono- & diglycerides, glyceryl monocaprylate, glyceryl tricaprylate/caprate/stearate, hydrogenated vegetable oil, hydrogenated cottonseed oil, hydrogenated soybean oil, hydrogenated soybean oil and castor wax, polyoxyethylene 8 caprylic/capric glycerides, polyoxyethylene 6 caprylic/capric glycerides, polyoxyethylene 32 lauric glycerides, polyoxyethylene 6 prop. glycol esters, polyoxyethylene 7 coconut glycerides, polyoxyethylene 30 coconut glycerides, polyoxyethylene 80 coconut glycerides, polyoxypropylene 15 stearyl ether, polyoxyethylene 26 glyceryl ether, polyoxyethylene 35 soybean glycerides, polyoxyethylene 20 sorbitol, polyoxypropylene 3 myristyl ether, polyoxypropylene 10 cetostearyl ether, palm kernelamide diethanolamide, triglycerol mono-oleate, sasol products, hydrogenated coco-glycerides, cetyl palmitate, trimyristin, tripalmitin, tristearin, hydrogenated palm oil, glyceryl monostearate, glyceryl stearate, cetearyl alcohol, cetyl alcohol, capric triglyceride, acetylated glycerides, glyceryl cocoate, and polyethylene glycol.

In other embodiments, the muscarinic antagonist component may further include a de-tackifier or glidant, such as talc, a monoglyceride, a diglyceride, glyceryl monostearate, calcium stearate, and magnesium stearate.

In still other embodiments, the immediate release muscarinic antagonist is formulated as beads including a core with muscarinic antagonist or a pharmaceutically acceptable salt thereof (e.g., oxybutynin or oxybutynin HCl) layered on top of the core. In some embodiments, the core comprises between about 10% to about 90% of the total weight of the finally-formulated bead. In some embodiments, the core comprises between about 25% to about 85% of the total weight of the finally-formulated bead. In some embodiments, the core comprises between about 40% to about 80% of the total weight of the finally-formulated bead. In some embodiments, the core comprises about 80% of the total weight of the finally-formulated bead. In some embodiments, the core comprises about 75% of the total weight of the finally-formulated bead. In some embodiments, the core comprises about 85% of the total weight of the finally-formulated bead.

In some embodiments, a solution of the muscarinic antagonist or a pharmaceutically acceptable salt thereof, is prepared and then sprayed onto the core and then dried. The act of spraying and drying causes a layer of the muscarinic antagonist or a pharmaceutically acceptable salt thereof to form over the bead. In some embodiments, the solution comprises a polymer that causes the muscarinic antagonist or a pharmaceutically acceptable salt thereof to more efficiently adhere to the core. The amount of the muscarinic antagonist or a pharmaceutically acceptable salt thereof present in the dosage form can be controlled by controlling the thickness of the layer. The thicker the layer the more muscarinic antagonist or a pharmaceutically acceptable salt thereof is present in the dosage form. Once the layer of muscarinic antagonist or a pharmaceutically acceptable salt thereof is exposed to aqueous media (e.g., gastric or intestinal juice), the muscarinic antagonist or a pharmaceutically acceptable salt thereof immediately dissolves into the aqueous medium.

In some embodiments, the layer of muscarinic antagonist or a pharmaceutically acceptable salt thereof comprises between about 1% to about 50% of the total weight of the bead. In some embodiments, the layer of muscarinic antagonist or a pharmaceutically acceptable salt thereof comprises between about 2% to about 40% of the total weight of the bead. In some embodiments, the layer of muscarinic antagonist or a pharmaceutically acceptable salt thereof comprises between about 4% to about 25% of the total weight of the bead. In some embodiments, layer of muscarinic antagonist or a pharmaceutically acceptable salt thereof comprises between about 5% to about 15% of the total weight of the bead. In some embodiments, the layer of muscarinic antagonist or a pharmaceutically acceptable salt thereof comprises between about 5.5% to about 10% of the total weight of the bead. In some embodiments, the layer of muscarinic antagonist or a pharmaceutically acceptable salt thereof comprises about 6% of the total weight of the bead. In some embodiments, the layer of muscarinic antagonist or a pharmaceutically acceptable salt thereof comprises about 6.5% of the total weight of the bead. In some embodiments, the layer of muscarinic antagonist or a pharmaceutically acceptable salt thereof comprises about 7% of the total weight of the bead. In some embodiments, the layer of muscarinic antagonist or a pharmaceutically acceptable salt thereof comprises about 8% of the total weight of the bead.

The muscarinic antagonist or a pharmaceutically acceptable salt thereof may be layered onto the core with a film-forming polymer, such as cellulose, hydroxyethylcellulose, hydroxypropylcellulose, hydroxypropylmethylcellulose, carboxymethylcellulose, maltodextrin, sucrose, modified starch, a salt of alginic acid, soluble gums, carrageenan, polyvinylpyrrolidone (PVP) or polyvinylpolypyrrolidone (PVPP), ethylcellulose, cellulose acetate phthalate, hydroxypropylmethylcellulose phthalate, insoluble gums, polymethacrylate, a polyvinyl alcohol, shellac, and polyvinyl acetate phthalate.

The layer of muscarinic antagonist or a pharmaceutically acceptable salt thereof may also contain a lipid excipient, a detackifier and a glidant, as described above.

In some embodiments, the delayed onset immediate release muscarinic agonist or a pharmaceutically acceptable salt thereof (e.g., pilocarpine or pilocarpine HCl) is formulated such that 20% or less of the muscarinic agonist or a pharmaceutically acceptable salt thereof (e.g., pilocarpine or pilocarpine HCl) in the composition is released approximately 20 minutes after administration to the subject and 75% or more of the muscarinic agonist or a pharmaceutically acceptable salt thereof in the composition is released approximately 30 minutes thereafter. In these embodiments, 20% or less of the muscarinic agonist or a pharmaceutically acceptable salt thereof (e.g., pilocarpine or pilocarpine HCl) in the composition is released approximately 20 minutes after administration to the subject, such as 15% or less, such as 10% or less, such as 5% or less, such as 3% or less and including 1% or less of the muscarinic agonist or a pharmaceutically acceptable salt thereof (e.g., pilocarpine or pilocarpine HCl) is released approximately 20 minutes after administration to the subject. After 20 minutes, the delayed onset immediate release muscarinic agonist or a pharmaceutically acceptable salt thereof is formulated to release 75% or more of the muscarinic agonist or a pharmaceutically acceptable salt thereof approximately 30 minutes thereafter, such as 80% or more, such as 85% or more, such as 90% or more, such as 95% or more, such as 97% or more and including 99% or more. In certain embodiments, 20 minutes after administration, the composition is formulated to release 100% of the muscarinic agonist approximately 30 minutes thereafter.

Figure 2:
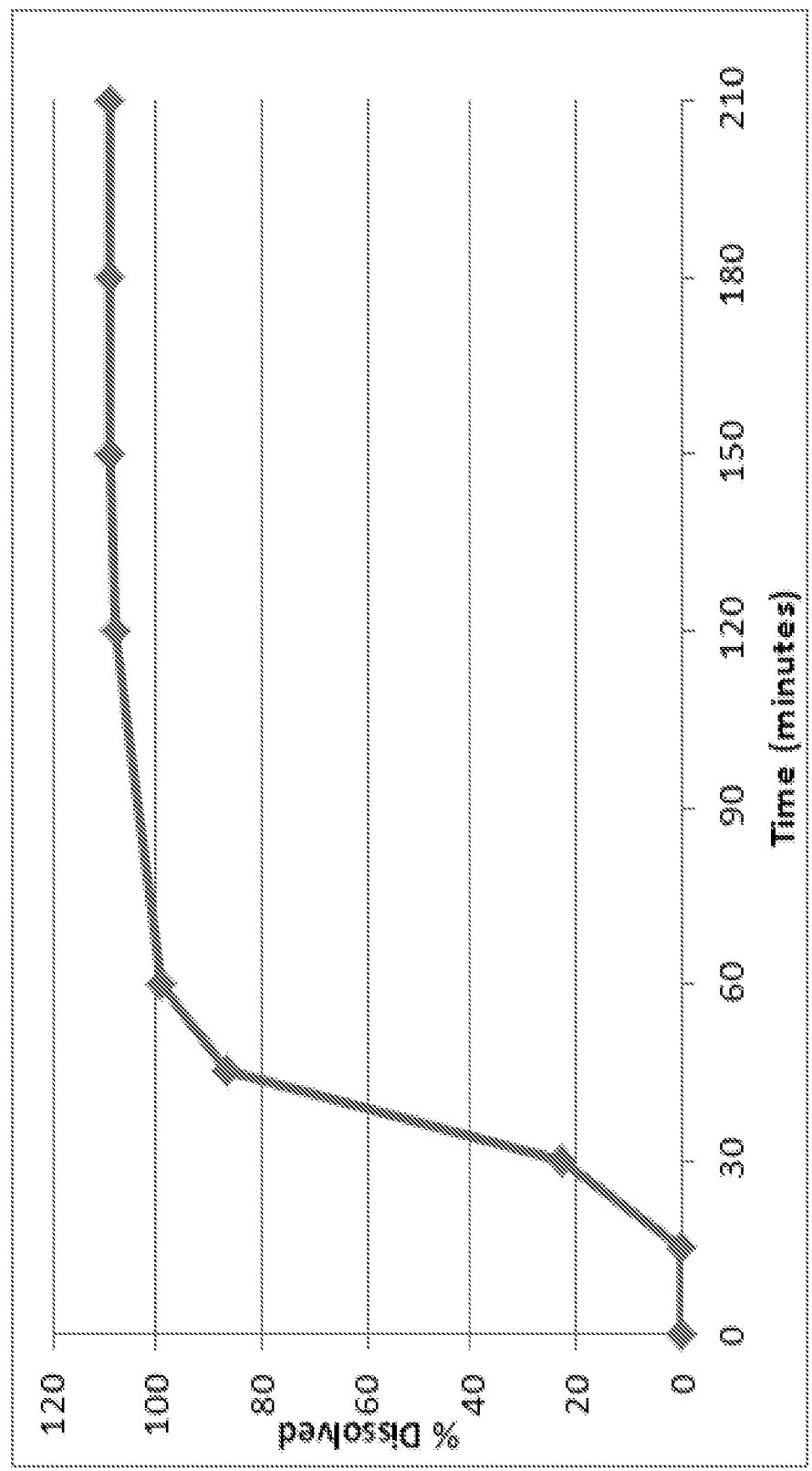
FIG. 2 depicts the dissolution profile of delayed onset immediate release pilocarpine beads according to one embodiment.

In certain embodiments, the delayed onset immediate release muscarinic agonist or pharmaceutically acceptable salt thereof is formulated to release the muscarinic agonist according to a release profile as generally depicted in FIG. 2.

In certain embodiments, the delayed onset immediate release muscarinic agonist or a pharmaceutically acceptable salt thereof is formulated as beads including a core with a first layer of muscarinic agonist or a pharmaceutically acceptable salt thereof (e.g., pilocarpine or pilocarpine HCl) coated on top of the core and a second layer including at least one polymer coated on top of the muscarinic agonist or a pharmaceutically acceptable salt thereof-containing layer.

In these embodiments, the core may include, but is not limited to, sugar beads (for example, Paular spheres), microcrystalline cellulose, Cellets® cores, such as Cellets® 100, Cellets® 200, Cellets® 350, Cellets® 500, Cellets® 700, or Cellets® 1000 (Glatt Air Techniques Inc., Ramsey N.J.). In other embodiments, the core is prepared de novo, for example by preparing a polymer mixture, extruding the mixture, and spheronizing the extruded mixture to form spherical or semi-spherical beads. In some embodiments, the beads are swellable such that their exposure to aqueous media causes them to swell and release the active ingredient rapidly and efficiently. In some embodiments, the core comprises between about 10% to about 50% of the total weight of the finally-formulated bead. In some embodiments, the core comprises between about 15% to about 40% of the total weight of the finally-formulated bead. In some embodiments, the core comprises between about 20% to about 30% of the total weight of the finally-formulated bead. In some embodiments, the core comprises about 20% of the total weight of the finally-formulated bead. In some embodiments, the core comprises about 25% of the total weight of the finally-formulated bead. In certain embodiments, the core includes a Cellets 700 microcrystalline cellulose bead.

In some embodiments, a first layer including a muscarinic agonist or a pharmaceutically acceptable salt thereof (e.g., pilocarpine or pilocarpine HCl) is formed on the core. In some embodiments, the first layer comprises between about 1% to about 50% of the total weight of the bead. In some embodiments, the first layer comprises between about 2% to about 40% of the total weight of the bead. In some embodiments, the first layer comprises between about 5% to about 30% of the total weight of the bead. In some embodiments, the first layer comprises between about 7% to about 25% of the total weight of the bead. In some embodiments, the first layer comprises between about 8% to about 15% of the total weight of the bead. In some embodiments, the first layer comprises about 8% of the total weight of the bead. In some embodiments, the first layer comprises about 10% of the total weight of the bead. In some embodiments, the first layer comprises about 12% of the total weight of the bead.

In some embodiments, the first layer comprises about 15% of the total weight of the bead.

In certain embodiments, the first layer containing the muscarinic agonist or a pharmaceutically acceptable salt thereof further includes a polymer such as cellulose, hydroxyethylcellulose, hydroxypropylcellulose, hydroxypropylmethylcellulose, carboxymethylcellulose, maltodextrin, sucrose, modified starch, a salt of alginic acid, soluble gums, carrageenan, polyvinylpyrrolidone (PVP) or polyvinylpolypyrrolidone (PVPP), ethylcellulose, cellulose acetate phthalate, hydroxypropylmethylcellulose phthalate, insoluble gums, polymethacrylate, a polyvinyl alcohol, shellac, and polyvinyl acetate phthalate and combinations thereof.

In some embodiments, the first layer containing the muscarinic agonist or a pharmaceutically acceptable salt thereof may further include a de-tackifier or glidant, such as talc, a monoglyceride, a diglyceride, glyceryl monostearate, calcium stearate, and magnesium stearate.

In other embodiments, the first layer containing the muscarinic agonist or a pharmaceutically acceptable salt thereof includes a lipid excipient, such as glyceryl behenate, glycerol esters of fatty acids, glyceryl dibehenate, behenoyl macrogoglycerides, glyceryl distearate, glycerol distearate, glyceryl palmitostearate, lauroyl macrogoglycerides, stearoyl macrogoglycerides, abitec products, glyceryl monooleate, medium chain mono- & diglycerides, glyceryl monocaprylate, glyceryl tricaprylate/caprate/stearate, hydrogenated vegetable oil, hydrogenated cottonseed oil, hydrogenated soybean oil, hydrogenated soybean oil and castor wax, polyoxyethylene 8 caprylic/capric glycerides, polyoxyethylene 6 caprylic/capric glycerides, polyoxyethylene 32 lauric glycerides, polyoxyethylene 6 prop. Glycol esters, polyoxyethylene 7 coconut glycerides, polyoxyethylene 30 coconut glycerides, polyoxyethylene 80 coconut glycerides, polyoxypropylene 15 stearyl ether, polyoxyethylene 26 glyceryl ether, polyoxyethylene 35 soybean glycerides, polyoxyethylene 20 sorbitol, polyoxypropylene myristyl ether, polyoxypropylene 10 cetostearyl ether, palm kernelamide diethanolamide, triglycerol mono-oleate, sasol products, hydrogenated coco-glycerides, cetyl palmitate, trimyristin, tripalmitin, tristearin, hydrogenated palm oil, glyceryl monostearate, glyceryl stearate, cetearyl alcohol, cetyl alcohol, capric triglyceride, acetylated glycerides, glyceryl cocoate, and polyethylene glycol or combinations thereof.

In certain embodiments, the first layer containing the muscarinic agonist or a pharmaceutically acceptable salt thereof includes pilocarpine or a pharmaceutically acceptable salt thereof, hydroxypropyl methylcellulose and talc.

In some embodiments, delayed onset immediate release formulations of muscarinic agonists or pharmaceutically acceptable salts thereof include a polymer layer (second layer) formed on top of the muscarinic agonist or a pharmaceutically acceptable salt thereof layer. Suitable polymers may include, but are not limited to, cellulose, hydroxyethylcellulose, hydroxypropylcellulose, hydroxypropylmethylcellulose, carboxymethylcellulose, maltodextrin, sucrose, modified starch, a salt of alginic acid, soluble gums, carrageenan, polyvinylpyrrolidone (PVP) or polyvinylpolypyrrolidone (PVPP), ethylcellulose, cellulose acetate phthalate, hydroxypropylmethylcellulose phthalate, insoluble gums, polymethacrylate, a polyvinyl alcohol, shellac, and polyvinyl acetate phthalate and combinations thereof. In some embodiments, the second layer comprises between about 1% to about 50% of the total weight of the bead. In some embodiments, the second layer comprises between about 2% to about 40% of the total weight of the bead. In some embodiments, the second layer comprises between about 5% to about 30% of the total weight of the bead. In some embodiments, the second layer comprises between about 7% to about 25% of the total weight of the bead. In some embodiments, the second layer comprises between about 8% to about 15% of the total weight of the bead. In some embodiments, the second layer comprises about 8% of the total weight of the bead. In some embodiments, the second layer comprises about 10% of the total weight of the bead. In some embodiments, the second layer comprises about 12% of the total weight of the bead. In some embodiments, the second layer comprises about 15% of the total weight of the bead.

In certain embodiments, the polymer layer coated on the muscarinic agonist or a pharmaceutically acceptable salt thereof layer includes ethylcellulose and hydroxypropylcellulose. The ratio of hydroxypropylcellulose to ethylcellulose may range between about 5:1 to about 1:5 by weight. In some embodiments, the ratio of hydroxypropylcellulose to ethylcellulose is between about 4:1 to about 1:4 by weight. In some embodiments, the ratio of hydroxypropylcellulose to ethylcellulose is between about 3:1 to about 1:3 by weight. In some embodiments, the ratio of hydroxypropylcellulose to ethylcellulose is between about 2:1 to about 1:2 by weight. In other embodiments, the ratio of ethylcellulose to hydroxypropylcellulose may range between about 5:1 to about 1:5 by weight. In some embodiments, the ratio of ethylcellulose to hydroxypropylcellulose is between about 4:1 to about 1:4 by weight. In some embodiments, the ratio of ethylcellulose to hydroxypropylcellulose is between about 3:1 to about 1:3 by weight. In some embodiments, the ratio of ethylcellulose to hydroxypropylcellulose is between about 2:1 to about 1:2 by weight. In some embodiments, the ratio of hydroxypropylcellulose to ethylcellulose is about 1:1 by weight.

In some embodiments, the polymer layer coated on the muscarinic agonist or a pharmaceutically acceptable salt thereof layer includes a plasticizer, such as a phthalate-based plasticizer, a trimellitate, an adipate-based plasticizer, a sebacate-based plasticizer, an organophosphate, a maleate, a sulfonamide, a glycols or polyether, an acetylated monoglyceride, and an alkyl citrate. The plasticizer may be present in between about 1% to about 50% of the total weight of the bead. In some embodiments, the plasticizer is present in between about 2% to about 40% of the total weight of the bead. In some embodiments, the plasticizer is present in between about 3% to about 20% of the total weight of the bead. In some embodiments, the plasticizer is present in between about 4% to about 10% of the total weight of the bead. In some embodiments, the plasticizer is present in about 4% of the total weight of the bead. In some embodiments, the plasticizer is present in about 4.5% of the total weight of the bead. In some embodiments, the plasticizer is present in about 5% of the total weight of the bead. In some embodiments, the plasticizer is present in about 5.5% of the total weight of the bead. In some embodiments, the plasticizer is present in about 6% of the total weight of the bead. In some embodiments, the plasticizer is present in about 6.5% of the total weight of the bead.

For example, the phthalate-based plasticizer may be bis (2-ethylhexyl) phthalate (DEHP), diisononyl phthalate (DINP), bis(n-butyl)phthalate (DnBP, DBP), butyl benzyl phthalate (BBzP), diisodecyl phthalate (DIDP), di-n-octyl phthalate (DOP or DnOP), diisooctyl phthalate (DIOP), diethyl phthalate (DEP), diisobutyl phthalate (DIBP), and di-n-hexyl phthalate. In some embodiments, the trimellitate is selected from the group consisting of trimethyl trimellitate (TMTM), tri-(2-ethylhexyl) trimellitate (TEHTM-MG), tri-(n-octyl,n-decyl) trimellitate (ATM), tri-(heptyl,nonyl) trimellitate (LTM), and n-octyl trimellitate (OTM). In some embodiments, the adipate-based plasticizer is selected from the group consisting of bis(2-ethylhexyl)adipate (DEHA), dimethyl adipate (DMAD), monomethyl adipate (MMAD), and dioctyl adipate (DOA). In some embodiments, the sebacate-based plasticiser is dibutyl sebacate (DBS). In some embodiments, the maleate is dibutyl maleate (DBM) or diisobutyl maleate (DIBM). In some embodiments, the sulfonamide is selected from the group consisting of ortho or para N-ethyl toluene sulfonamide (ETSA), N-(2-hydroxypropyl)benzene sulfonamide (HP BSA), and N-(n-butyl) benzene sulfonamide (BBSA-NBBS). In some embodiments, the organophosphate is tricresyl phosphate (TCP) or tributyl phosphate (TBP). In some embodiments, the glycol or polyether is selected from the group consisting of triethylene glycol dihexanoate (3G6, 3 GH), tetraethylene glycol diheptanoate (4G7), and polyethylene glycol. In some embodiments, the alkyl citrate is selected from the group consisting of Triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC, trihexyl o-butyryl citrate), and trimethyl citrate (TMC). In some embodiments, the plasticizer is selected from the group consisting of dibutyl sebacate, polyethylene glycol, glycerin, triacetin, diethyl phthalate, propylene glycol, triethyl citrate, mineral oil, an acetylated monoglyceride, and oleic acid. In certain embodiments, the layer on top of the muscarinic agonist layer includes dibutyl sebacate.

In some embodiments, the weight of the second layer is between about 50% to about 300% of the weight of the bead prior to the application of the second layer. In some embodiments, the weight of the second layer is between about 75% to about 250% of the weight of the bead prior to the application of the second layer. In some embodiments, the weight of the second layer is about 75% of the weight of the bead prior to the application of the second layer. In some embodiments, the weight of the second layer is about 100% of the weight of the bead prior to the application of the second layer. In some embodiments, the weight of the second layer is about 125% of the weight of the bead prior to the application of the second layer. In some embodiments, the weight of the second layer is about 150% of the weight of the bead prior to the application of the second layer. In some embodiments, the weight of the second layer is about 175% of the weight of the bead prior to the application of the second layer. In some embodiments, the weight of the second layer is about 200% of the weight of the bead prior to the application of the second layer. In some embodiments, the weight of the second layer is about 225% of the weight of the bead prior to the application of the second layer. In some embodiments, the weight of the second layer is about 250% of the weight of the bead prior to the application of the second layer.

In certain embodiments, the muscarinic agonist or a pharmaceutically acceptable salt thereof component of the subject compositions includes beads including:
 a microcrystalline core;
 a first layer coated on the microcrystalline core containing pilocarpine or a pharmaceutically acceptable salt thereof, hydroxypropyl methylcellulose and talc; and
 a second layer coated on the first layer containing ethylcellulose, hydroxypropylcellulose and dibuty sebacate.

In certain embodiments, the muscarinic agonist or a pharmaceutically acceptable salt thereof component of the subject compositions includes beads including:
 a microcrystalline core that is about 20% of the total weight of the bead
 a first layer on top of the microcrystalline core containing pilocarpine or a pharmaceutically acceptable salt thereof present in an amount that is about 8% of the total weight of the bead, hydroxypropyl methylcellulose present in an amount that is about 8% of the total weight of the bead and talc present in an amount that is about 4% of the total weight of the bead; and
 a second layer coated on the first layer containing ethylcellulose present in an amount that is about 26% of the total weight of the bead, hydroxypropylcellulose present in an amount that is about 26% of the total weight of the bead, and dibutyl sebacate present in an amount that is about 5% of the total weight of the bead.

In certain embodiments, the subject compositions containing a muscarinic antagonist or a pharmaceutically acceptable salt thereof and a muscarinic agonist or a pharmaceutically acceptable salt thereof are those described in United States Patent Publication No. 2011/0244051 filed on Apr. 1, 2011, the disclosure of which is herein incorporated by reference in its entirety.

In certain embodiments, the muscarinic agonist or pharmaceutically acceptable salt thereof is formulated as a mini-tablet including a core comprising the muscarinic agonist or pharmaceutically acceptable salt thereof and a coating layer that includes a coating polymer.

In some embodiments, the core comprises between about 70% to about 99% of the total weight of the finally-formulated mini-tablet. In some embodiments, the core comprises between about 75% to about 97% of the total weight of the finally-formulated mini-tablet. In some embodiments, the core comprises between about 80% to about 95% of the total weight of the finally-formulated mini-tablet. In some embodiments, the core comprises between about 85% to about 95% of the total weight of the finally-formulated mini-tablet. In some embodiments, the core comprises between about 88% to about 95% of the total weight of the finally-formulated mini-tablet.

In some embodiments, a stock solution comprising the muscarinic agonist (e.g., pilocarpine) or a pharmaceutically acceptable salt thereof, and a polymer is prepared and then sprayed onto a fluidized bed, using methodology well-known in the art. In some embodiments, the fluidized bed is a cellulose bed. In some of these embodiments, the fluidized bed is a microcrystalline cellulose bed. In further embodiments, the fluidized bed is a silicified microcrystalline cellulose bed. In some embodiments, the fluidized bed is, for example, PROSOLV® SMCC, such as PROSOLV® SMCC 50.

In some embodiments, the core further includes an osmotic agent. The osmotic agent in certain instances causes the core to disintegrate rapidly and release the API as soon as the core comes into contact with an aqueous medium, such as the gastric or intestinal juice. In some embodiments, the osmotic agent is an inorganic salt. In some of these embodiments, the salt is a salt of an alkali metal. In further embodiments, the salt is a halide slat of an alkali metal. In some embodiments, the salt is selected from the group consisting of lithium chloride, lithium bromide, lithium iodide, sodium chloride, sodium bromide, sodium iodide, potassium chloride, potassium bromide, and potassium iodide.

In some embodiments, the core comprises a disintegrant. In some embodiments, the disintegrant is a cross-linked polymer. In some of these embodiments, the cross-linked polymer is cross-linked polyvinylpyrrolidone (crospovidone) or cross-linked sodium carboxymethyl cellulose (croscarmellose sodium). In other embodiments, the disintegrant is a modified starch, for example sodium starch glycolate.

In some embodiments, the core further includes a lubricant. In some embodiments, the lubricant is a mineral, such as talc or silica. In other embodiments, the lubricant is a fat, e.g., vegetable stearin, magnesium stearate, stearic acid, or a derivatized stearic acid. In some embodiments, the derivatized stearic acid is sodium stearyl fumarate.

In some embodiments, the muscarinic agonist or pharmaceutically acceptable salt thereof (e.g., pilocarpine or pharmaceutically acceptable salt thereof) is present in the core between about 0.1% to about 5% by weight of the core. In other embodiments, the muscarinic agonist or pharmaceutically acceptable salt thereof is present in the core between about 0.3% to about 4% by weight; or between about 0.5% to about 3% by weight.

In some embodiments, the fluidized bed, i.e., cellulose, in the core is present in between about 40% to about 75% by weight of the core, or between about 45% to about 70% by weight, or between about 48% to about 65% by weight of the core.

In some embodiments, the core polymer is present in between about 4% to about 15% by weight of the core, or between about 5% to about 12% by weight, or between about 5% to about 10% by weight of the core.

In some embodiments, the disintegrant is present in between about 5% to about 35% by weight of the core, or between about 5% to about 25% by weight, or between about 10% to about 30% by weight, or between about 10% to about 20% by weight, or between about 12% to about 17% by weight of the core.

In some embodiments, the salt is present in between about 10% to about 50% by weight of the core, or between about 10% to about 40% by weight, or between about 12% to about 37% by weight, or between about 15% to about 35% by weight of the core.

In some embodiments, the lubricant is present in between about 0.2% to about 2% by weight of the core, or between about 0.5% to about 1.7% by weight, or between about 0.5% to about 1.5% by weight of the core.

In mini-tablets of interest, the core is coated by a coating layer. In certain embodiments, the coating layer is formulated to delay the exposure of the core to aqueous media, for example gastric juice or intestinal fluid. The coating layer includes a coating polymer. In certain embodiments, the coating polymer is a cellulose polymer. In some of these embodiments, the cellulose polymer is microcrystalline cellulose. In other embodiments, the coating polymer is a derivatized cellulose, for example, alkylated cellulose. In some of these embodiments, the derivatized cellulose is selected from the group consisting of ethyl cellulose, propyl cellulose and hydroxylpropyl cellulose.

In some embodiments, the application of the coating layer causes a weight gain of between about 1% to about 50% of the weight of the mini-tablet prior to the application of the coating layer. Thus, for example, if the weight of the core prior to the application of the coating layer is X, then after the application of the coating layer, the weight of the mini-tablet is 1.01×, if the weight gain is 1%, or the weight of the mini-tablet is 1.5×, if the weight gain is 50%. In some embodiments, the weight gain is between about 5% to about 45%. In some embodiments, the weight gain is between about 5% to about 40%. In some embodiments, the weight gain is between about 5% to about 35%. In some embodiments, the weight gain is between about 5% to about 30%. In some embodiments, the weight gain is between about 10% to about 25%.

In some embodiments, the coating polymer includes a sugar or a polysaccharide. In some of these embodiments, the sugar or polysaccharide is selected from the group consisting of cellulose, hydroxyethylcellulose, hydroxypropylcellulose, hydroxypropylmethylcellulose, carboxymethylcellulose, maltodextrin, sucrose, modified starch, a salt of alginic acid, soluble gums, and carageenan. In other embodiments, the coating polymer comprises polyvinylpyrrolidone (PVP) or polyvinylpolypyrrolidone (PVPP).

In some embodiments, the coating polymer is a mixture of two or more polymers. In some embodiments, the mixture comprises ethylcellulose (EC) and hydroxypropylcellulose (HPC). In certain instances, EC is present in between about 60% to about 95% of the weight of the coating, or between about 60% to about 85% of the weight, or between about 61% to about 84% by weight, or between about 61% to about 82% by weight. In certain instances, HPC is present in between about 5% to about 35% of the weight of the coating, or between about 5% to about 20% of the weight, or between about 7% to about 17% by weight, or between about 7% to about 16% by weight.

In some embodiments, the coating further includes a lubricant. In some embodiments, the lubricant is a mineral, such as talc or silica. In some embodiments, the lubricant is present in between about 1% to about 20% of the weight of the coating, or between about 5% to about 17% by weight, or between about 10% to about 16% by weight.

In some embodiments, the coating further includes a plasticizer. In some embodiments, the plasticizer is selected from the group consisting of a phthalate-based plasticizer, a trimellitate, an adipate-based plasticizer, a sebacate-based plasticizer, an organophosphate, a maleate, a sulfonamide, a glycols or polyether, an acetylated monoglyceride, and an alkyl citrate. In some embodiments, the sebacate-based plasticiser is dibutyl sebacate (DBS). In some embodiments, the plasticizer is present in between about 1% to about 20% of the weight of the coating, or between about 5% to about 15% by weight, or between about 7% to about 10% by weight.

In certain embodiments, the subject mini-tablets containing a muscarinic agonist or a pharmaceutically acceptable salt thereof (e.g., pilocarpine or pharmaceutically acceptable salt thereof) are those described in United States Patent Publication No. 2014/0105976 filed on Oct. 11, 2013, the disclosure of which is herein incorporated by reference in its entirety.

Aspects, including embodiments, of the subject matter described herein may be beneficial alone or in combination, with one or more other aspects or embodiments. Without limiting the description, certain non-limiting aspects of the disclosure numbered 1-34 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of treating hyperhidrosis with a muscarinic antagonist and reducing a dry mouth side effect of the muscarinic antagonist in a subject in need thereof, the method comprising:
    administering to the subject a therapeutically effective amount of a composition comprising a muscarinic antagonist or a pharmaceutically acceptable salt thereof and a muscarinic agonist or a pharmaceutically acceptable salt thereof,
    wherein the administering is effective at reducing hyperhidrosis, and
    wherein the administering is sufficient to reduce a dry mouth side effect of the muscarinic antagonist.
2. The method according to 1, wherein the subject is diagnosed as having primary focal axillary hyperhidrosis.
3. The method according to 1, wherein the subject is diagnosed as having primary focal palmar hyperhidrosis.
4. The method according to 1, wherein the subject is diagnosed as having plantar hyperhidrosis.
5. The method according to 1, wherein the subject is diagnosed as having craniofacial hyperhidrosis.
6. The method according to 1, wherein the subject is diagnosed as having generalized hyperhidrosis.
The method according to 1, wherein the subject is diagnosed as having compensatory sweating post-surgery.
8. The method according to any one of 1-7, wherein the muscarinic antagonist is oxybutynin or a pharmaceutically acceptable salt thereof.
9. The method according to any one of 1-8, wherein the muscarinic agonist is pilocarpine or a pharmaceutically acceptable salt thereof.
10. The method according to 8 or 9, wherein the composition comprises from about 5 to about 30 mg of oxybutynin or a pharmaceutically acceptable salt thereof.
11. The method according to 10, wherein the composition comprises about 7.5 mg of oxybutynin or a pharmaceutically acceptable salt thereof.
12. The method according to 11, wherein the composition comprises about 5.0 mg of oxybutynin or a pharmaceutically acceptable salt thereof.
13. The method according to any one of 9-12, wherein the composition comprises from about 5 to about 30 mg of pilocarpine or a pharmaceutically acceptable salt thereof.
14. The method according to claim 13, wherein the composition comprises about 7.5 mg of pilocarpine or a pharmaceutically acceptable salt thereof.
15. The method according to 13, wherein the composition comprises about 5.0 mg of pilocarpine or a pharmaceutically acceptable salt thereof.
16. The method according to any one of 1-15, wherein the method comprises administering the composition once per day.
17. The method according to any one of 1-15, wherein the method comprises administering the composition twice per day.
18. The method according to any one of 1-15, wherein the method comprises administering the composition for one month or longer.
19. The method according to any one of 1-15, wherein the method comprises administering the composition for one year or longer.
20. The method according to any one of 8-19, wherein the composition comprises an immediate release composition comprising oxybutynin or a pharmaceutically acceptable salt thereof and a delayed onset immediate release composition comprising pilocarpine or a pharmaceutically acceptable salt thereof.
21. The method according to any one of 8-20, wherein the composition is formulated such that the peak plasma concentration of oxybutynin or a pharmaceutically acceptable salt thereof and the peak plasma concentration of pilocarpine or a pharmaceutically acceptable salt thereof in the subject occurs at approximately the same time.
22. The method according to 21, wherein the delayed onset immediate release composition is formulated such that less than 20% of the pilocarpine or a pharmaceutically acceptable salt thereof in the composition is released approximately 20 minutes after administration to the subject and 90% or more of the pilocarpine or a pharmaceutically acceptable salt thereof in the composition is released approximately 30 minutes thereafter.
23. The method according to 21, wherein the composition comprises:
    oxybutynin or a pharmaceutically acceptable salt thereof; and
    a plurality of pilocarpine beads, each pilocarpine bead comprising:
        a core;
        a first layer positioned over the core comprising pilocarpine or a pharmaceutically acceptable salt thereof; and
        a second layer positioned over the first layer comprising hydroxypropylcellulose and ethylcellulose.
24. The method according to 21, wherein the composition comprises:
    oxybutynin or a pharmaceutically acceptable salt thereof; and
    a plurality of pilocarpine mini-tablets, each pilocarpine mini-tablet comprising:
        a core comprising pilocarpine; and
        a coating layer comprising a coating polymer.
25. The method according to 24, wherein the coating layer comprises a sugar or a polysaccharide selected from the group consisting of cellulose, ethylcellulose (EC), hydroxyethylcellulose (HEC), hydroxypropylcellulose (HPC), hydroxypropylmethylcellulose (HPMC), carboxymethylcellulose, maltodextrin, sucrose, modified starch, a salt of alginic acid, soluble gums, carageenan, and a combination thereof.
26. The method according to 24, wherein the coating layer comprises polyvinylpyrrolidone (PVP) or polyvinylpolypyrrolidone (PVPP).
27. The method according to any one of 1-26, wherein dry mouth is reduced as determined by a dry mouth visual analog scale.
28. The method according to any one of 1-27 wherein dry mouth is reduced as reported by the subject with a dry mouth incidence/severity questionnaire.
29. The method according to any one of 1-28 wherein hyperhidrosis is reduced as measured on the hyperhidrosis disease severity scale.
30. The method according to any one of 1-29, wherein hyperhidrosis is reduced as measured by axillary, plantar or palmar gravimetric analysis.
31. The method according to any one of 1-30, wherein hyperhidrosis is reduced as measured by a hyperhidrosis visual quantification scale.

32. The method according to any one of 1-31, wherein hyperhidrosis is reduced as measured by a hyperhidrosis visual analog scale.

33. The method according to any one of 1-32, wherein hyperhidrosis is reduced as measured by transdermal epidural water vapor loss.

34. A method of treating hyperhidrosis with oxybutynin or a pharmaceutically acceptable salt thereof and reducing a dry mouth side effect of the oxybutynin with pilocarpine or a pharmaceutically acceptable salt thereof in a subject in need thereof, the method comprising:
administering to the subject a therapeutically effective amount of a composition comprising 5 to 30 mg of oxybutynin or a pharmaceutically acceptable salt thereof and 5 to 30 mg pilocarpine or a pharmaceutically acceptable salt thereof,
wherein the composition is formulated such that the peak plasma concentration of oxybutynin or a pharmaceutically acceptable salt thereof and the peak plasma concentration of pilocarpine or a pharmaceutically acceptable salt thereof in the subject occurs at approximately the same time,
wherein the administering is at least as effective at reducing hyperhidrosis in the subject as administration of oxybutynin or a pharmaceutically acceptable salt thereof alone, and
wherein the administering is sufficient to reduce a dry mouth side effect of the oxybutynin or a pharmaceutically acceptable salt thereof.

The following examples are offered by way of illustration and not by way of limitation. Specifically, the following examples are of specific embodiments for carrying out the present disclosure. The examples are for illustrative purposes only, and are not intended to limit the scope of the present disclosure in any way. Efforts have been made to ensure accuracy with respect to numbers used (e.g., amounts, temperatures, etc.), but some experimental error and deviation should, of course, be allowed for.

EXPERIMENTAL

Preparation of Example Muscarinic Antagonist and Muscarinic Agonist Formulations Capsules containing a muscarinic antagonist component and a muscarinic agonist component were prepared. The muscarinic antagonist (oxybutynin—as oxybutynin HCl) was prepared as a granulate and the muscarinic agonist (pilocarpine—as pilocarpine HCl) was prepared as multilayer beads. Capsules containing 7.5 mg of oxybutynin HCl granulate and 7.5 mg of pilocarpine HCl multilayer beads were prepared as described below.

Active Agents

Oxybutynin HCl is a white crystalline powder. Pilocarpine HCl is a white to almost white crystalline powder.

Materials

Table 1 lists the compounds used in the preparing capsules containing a muscarinic antagonist component and a muscarinic agonist component.

TABLE 1

| Generic Name | Trade Name |
| --- | --- |
| Oxybutynin HCl | — |
| Pilocarpine HCl | — |
| Povidone K-29/32 | Plasdone K29/32 |

TABLE 1-continued

| Generic Name | Trade Name |
| --- | --- |
| Silicified Microcrystalline Cellulose | Prosolv SMCC 50 |
| Microcrystalline Cellulose Beads | Cellets 700 |
| Hydroxypropyl Methylcellulose (HPMC) | Pharmacoat 606 |
| Talc | Pharma 400 |
| Ethylcellulose | Aqualon EC-N10 |
| Hydroxypropyl Cellulose | Klucel EXF |
| Dibutyl Sebacate | — |
| 200 Proof Ethanol | — |
| White Opaque Gelatin Capsules, Size 0 | Coni-Snap |
| Sterile water | — |

Pilocarpine Beads

Inert microcrystalline cellulose beads were coated with two layers: a drug layer containing immediate release pilocarpine HCl, and a delayed release polymer layer. The overall formulation for the pilocarpine delayed onset immediate release beads is summarized in Table 2. FIG. 1 illustrates the process for manufacturing the pilocarpine beads with the components listed in Table 2. Tables 3-4 provides process parameters for preparing the pilocarpine beads.

TABLE 2

| Component | Chemical Name | Description | % w/w | mg/dose |
| --- | --- | --- | --- | --- |
| Core | Microcrystalline cellulose pellets | Coating substrate | 20.8 | 18.75 |
| Muscarinic Agonist | Pilocarpine HCl | Active Agent | 8.3 | 7.5 |
| Muscarinic Agonist Layer | Hydroxypropyl Methylcellulose | Film former | 8.3 | 7.5 |
| Muscarinic Agonist Layer | Talc | De-tackifier | 4.2 | 3.75 |
| Release Layer | Hydroxylpropyl Cellulose | Film Former | 26.5 | 23.83 |
| Release Layer | Ethylcellulose | Film Former | 26.5 | 23.83 |
| Release Layer | Dibutyl Sebacate | Plasticizer | 5.3 | 4.77 |

TABLE 3

Fluid Bead Pilocarpine Layering

| Equipment | Vector FLM1 |
| --- | --- |
| Batch size | 0.70 kg |
| Process air | 45-50 CFM |
| Spray rate | 12-17 g/min. |
| Atmospheric Air Pressure | 37 psi |
| Inlet Temperature | 82 ± 5° C. |
| Product Temperature | 50 ± 2° C. |
| Dew Point | 10° C. |

TABLE 4

Fluid Bead Release Polymer Layering

| Equipment | Vector FLM1 |
| --- | --- |
| Batch size | 0.53 kg |
| Process air | 58-60 CFM |
| Spray rate | 22-30 g/min. |
| Atmospheric Air Pressure | 40 psi |
| Inlet Temperature | 52 ± 5° C. |
| Product Temperature | 35 ± 2° C. |
| Dew Point | 8° C. |

The pilocarpine beads prepared were tested for dissolution in 0.1 N HCl to and provide a delayed onset immediate release profile for pilocarpine. FIG. 2 depicts the dissolution profile of beads prepared according to Table 2.

Oxybutynin Granulate

Figure 3:
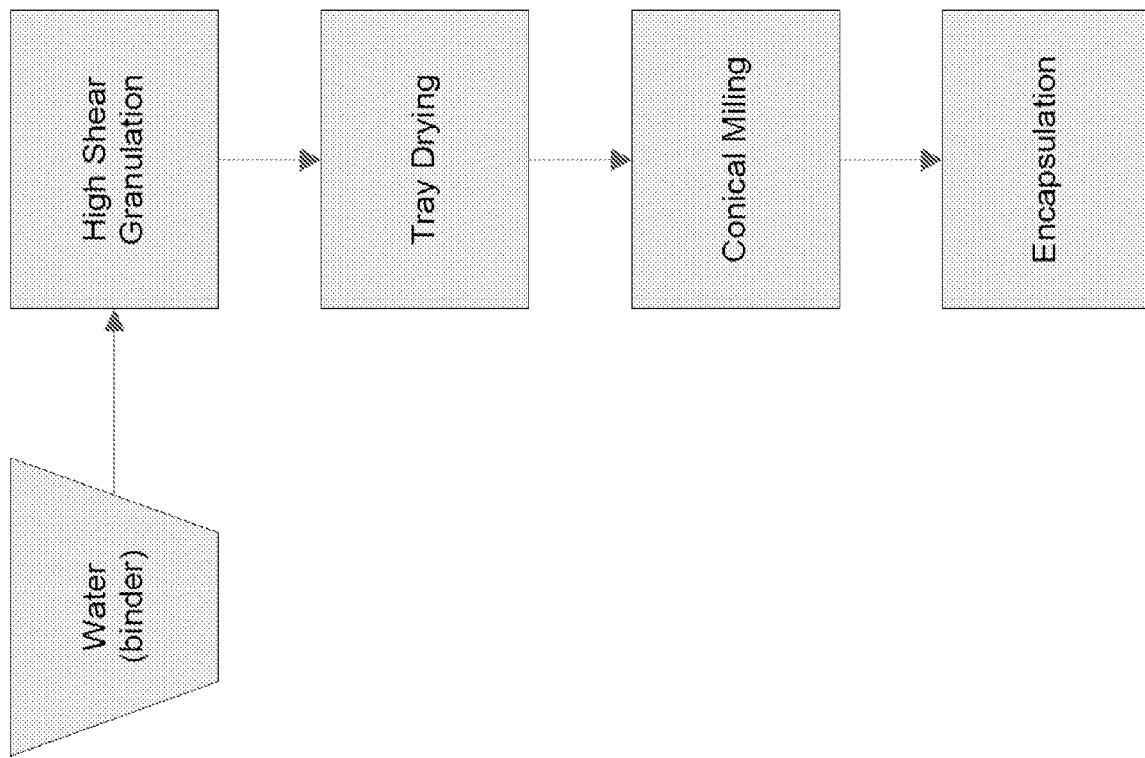
FIG. 3 illustrates a process for manufacturing an oxybutynin granulate according to one embodiment.

A high shear oxybutynin HCl granulation was prepared. The overall formulation for the oxybutynin HCl immediate release granulate is summarized in Table 5. FIG. 3 illustrates the process for manufacturing the oxybutynin granulate with the components listed in Table 5. Table 6 provides process parameters for preparing the oxybutynin granulate.

TABLE 5

| Component | Chemical Name | Description | % w/w | mg/dose |
|---|---|---|---|---|
| Muscarinic Antagonist | Oxybutynin HCl | Active Agent | 18.75 | 7.5 |
| Polymer | Polyvinylpyrrolidone | Binder | 3.75 | 1.5 |
| Polymer | Silicified microcrystalline cellulose | Binder | 77.50 | 31.0 |

TABLE 6

| High Shear Granulation | |
|---|---|
| Equipment | Vector GMX 4L |
| Batch size | 0.90 kg |
| Process air | 58-60 CFM |
| Muscarinic Antagonist/Binder Solution | Water |
| Impeller Speed | 547 rpm |
| Chopper Speed | 1800 rpm |
| Tray Drying | |
| Temperature | 50° C. |
| Drying Time | 8 hours |
| Final LOD % | 1.91% |
| Milling | |
| Equipment | Quadro Comil 197S |
| Batch size | 0.89 kg |
| Screen | 24R |
| Impeller | Square |
| Impeller speed | 3000 rpm |

Figure 4:
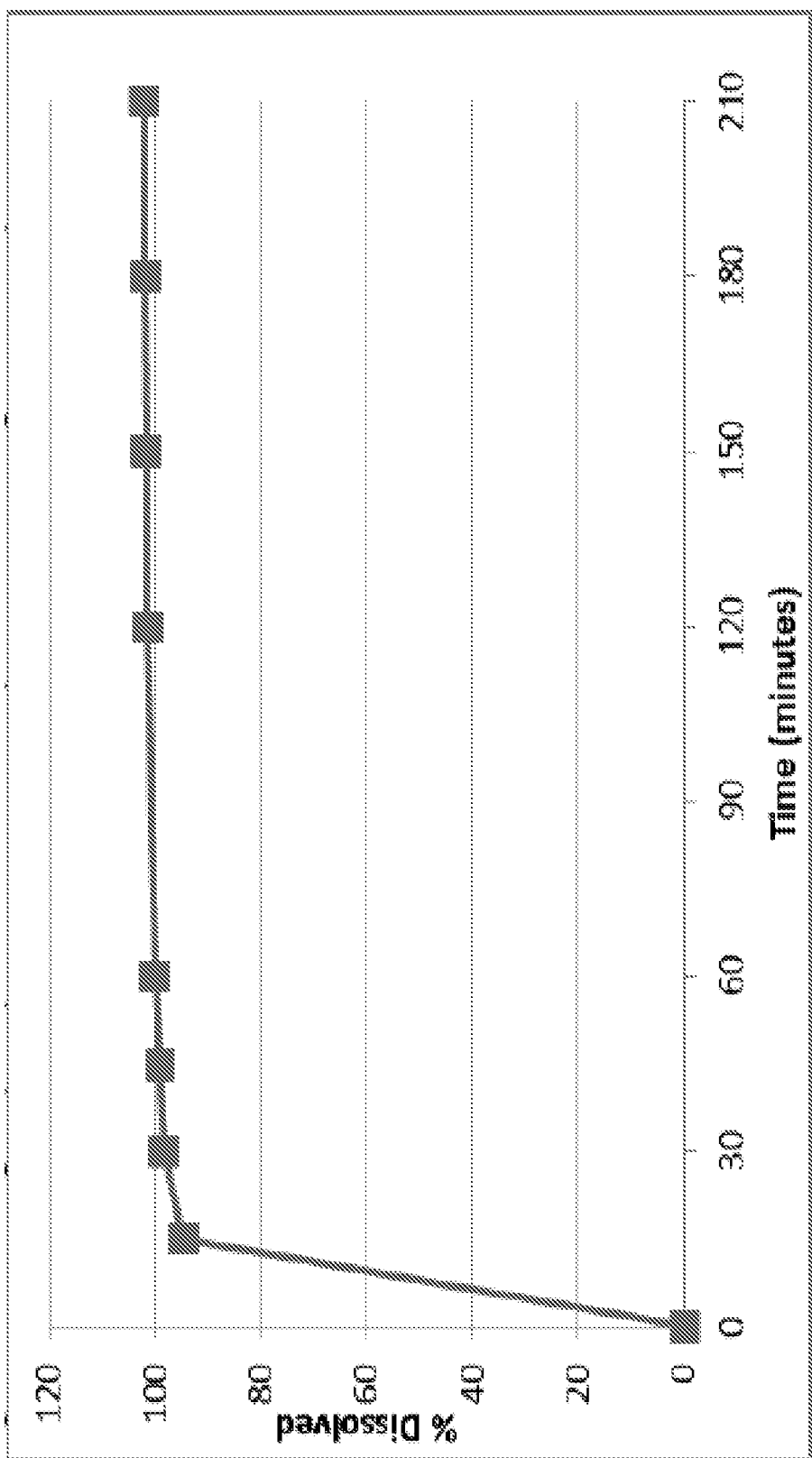
FIG. 4 depicts the dissolution profile of an immediate release oxybutynin granulate in a gelatin capsule according to one embodiment.

The oxybutynin granulate was hand filled into size 0 gelatin capsules which were tested for dissolution in 0.1 N HCl to and provided an immediate release profile for oxybutynin. FIG. 4 depicts the dissolution profile of the oxybutynin granulate prepared according to Table 5.

Compositions for Treating Hyperhidrosis with Oxybutynin and Pilocarpine

The coated pilocarpine HCl beads and oxybutynin HCl granulate described above were encapsulated into size 0 gelatin capsules. Table 7 summarizes the formulation prepared for treating hyperhidrosis.

TABLE 7

| Component | % w/w | mg/dose |
|---|---|---|
| Oxybutynin HCl Granulate | 17.7 | 40.0 |
| Pilocarpine HCl Beads | 39.8 | 89.9 |
| Size 0 white gelatin capsule | 4.25 | 96.0 |

Each capsule was partially filled with the oxybutynin HCl granulate using a Xcelodose 120S semi-automatic encapsulator. Capsules were partially filled in groups of 10 by the Xcelodose. 89.9 mg of pilocarpine HCl beads were weighed and manually filled into each capsule. A cap was manually placed onto each capsule and each capsule was manually closed. THVD-102 [7.5/7.5] is a composition as prepared in this example for treating subjects with hyperhidrosis (as described in greater detail below) that contains 7.5 mg of oxybutynin HCl and 7.5 mg of pilocarpine HCl.

Treatment of Hyperhidrosis with a Therapeutically Effective Amount of a Composition Including a Muscarinic Antagonist and Muscarinic Agonist Clinical Study Objectives One objective of the study includes evaluating the safety and efficacy of THVD-102 [7.5/7.5] (a composition including oxybutynin and pilocarpine as prepared above) in subjects with primary focal hyperhidrosis (e.g., axillary and/or palmar). Another objective of the study includes evaluating dry mouth and quality of life in subjects receiving THVD-102 [7.5/7.5] (oxybutynin plus pilocarpine).

Clinical Study Design

Figure 5:
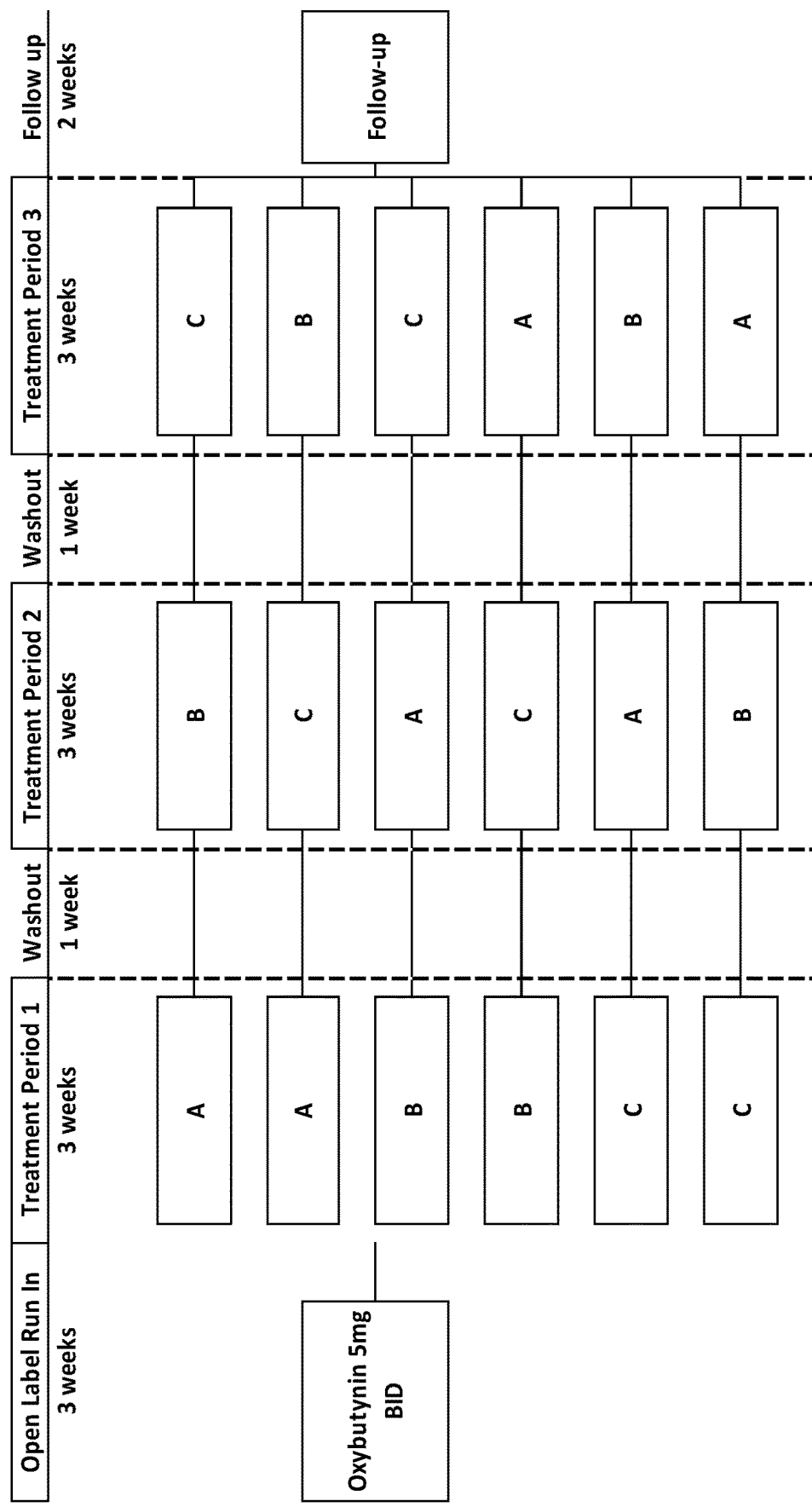
FIG. 5 illustrates a scheme for a clinical study design for administering to a group of subjects a composition of oxybutynin and pilocarpine according to one embodiment.

The clinical study was a randomized, double blind, placebo-controlled, crossover study of approximately 18 subjects. Following qualification, subjects were randomized to one of 6 groups/sequences during which they received each of the three study treatments in sequential treatment periods. Each 21-day double-blind study treatment period was preceded by an at least 7-day washout period. Subsequent study treatment assignments were via the sequential three-way crossover design prescribed in that group. After completing the final study treatment period or early study treatment discontinuation, all subjects completed an end of study visit (approximately 14 days after the last study treatment administration. FIG. 5 illustrates a scheme of the clinical study design.

As described above, this was a cross-over design study in which all subjects were to receive all 3 of the study treatments (1 in each of the 3 double-blind treatment periods). The use of the crossover design allowed a smaller number of subjects and introduced lower variability as each subject acted as his/her own control.

The study was preceded by an Oxybutynin Run-in Period during which subjects received oxybutynin 5 mg twice daily by mouth; this was incorporated to help identify subjects who had anti-muscarinic induced dry mouth that could be measured using the Dry Mouth Visual Analog Scale (DM-VAS). A minimum score of 25 mm on a 100 mm scale was required on the DMVAS.

Placebo was used as the comparator for safety and the comparator for efficacy in hyperhidrosis; THVD-102 [7.5/7.5] and oxybutynin were both compared to placebo. The active control of oxybutynin 7.5 mg is the comparator for THVD-102 [7.5/7.5] for the anti-muscarinic induced dry mouth symptom incidence and severity.

Subjects were randomized to 1 of 6 groups/sequences of study treatment administration. Each sequence included sequential crossover assignment to a 21-day treatment period of:
  oxybutynin 7.5 mg BID alone by mouth;
  THVD-102 [7.5/7.5] (oxybutynin 7.5 mg in combination with pilocarpine 7.5 mg) BID by mouth; and
  placebo BID by mouth.

To be included in the clinical study, subjects must have met all eligibility criteria, including a Hyperhidrosis Disease Severity Scale (HDSS) score of 3 or 4 on Day 1 of Treatment Period 1 and a DMVAS score of at least 25 mm following the run-in period of open-label oxybutynin. Initially, 3 to 4 subjects were randomized to each group/sequence for a total of 21 to ensure at least 18 completed subjects. Subjects who do not complete all 3 three double-blind treatment periods were replaced.

Following qualification, subjects were randomized to one of 6 groups/sequences during which they were to receive each of the 3 study treatments in sequential 21-day double-blind treatment periods. Each double-blind treatment period was preceded by a washout period of at least 7 days.

Subsequent study treatment assignments were assigned according to the sequential three-way cross-over design prescribed for the group to which the subject was assigned. The study treatment assignments are summarized in Table 8.

TABLE 8

| | Study Treatment Assignment | | |
|---|---|---|---|
| Group | Treatment Period 1 | Treatment Period 2 | Treatment Period 3 |
| 1 | A | B | C |
| 2 | A | C | B |
| 3 | B | A | C |
| 4 | B | C | A |
| 5 | C | A | B |
| 6 | C | B | A |
| Total | 18 | 18 | 18 |

Subjects were randomized and enrolled following confirmation of eligibility. All subjects received the same dose of THVD-102 [7.5/7.5] and oxybutynin. Subjects were instructed to take the study treatment at approximately the same times of day (e.g. 7:00 am and 7:00 pm). All study visits were conducted at approximately the same time of day to avoid diurnal variation in study assessments and to allow at least 4 hours from the time of study treatment administration on that morning, if applicable. Subjects were instructed to take the morning dose of study treatment as scheduled prior to Day 21 assessments. If a subject missed a planned study drug administration, it was to be taken anytime during that calendar day; subjects were instructed not to administer study treatment more than 2 times each calendar day and not within 6 hours of the previous administration. The 12-hour interval between study drug administrations was intended to provide a close to 24-hour period of coverage and consistent dose intensity.

Study drug compliance was assessed at each visit when unused study drug was returned. The amount of study drug returned was compared with the amount of study drug dispensed and that was expected to have been administered. Subjects with inadequate study drug compliance (<80%) may have been discontinued from study treatment.

Subjects returned to the investigational site for safety and efficacy assessments at the end of each treatment period (Day 21); subsequent treatment periods began at least 7 days following the end of the preceding period to allow a sufficient washout period.

At the conclusion of all 3 treatment periods (or in the case of early study treatment discontinuation), subjects returned to the investigational site for safety assessments approximately 14 days following the last study treatment administration for follow-up (End of Study Visit).

Study assessments for efficacy/activity included:
Hyperhidrosis Disease Severity Scale (HDSS)
Gravimetric assessments (axillary [paper] &/or palmar [paper+glove])
Rate of water vapor loss using a closed chamber device; Delfin VapoMeter
Hyperhidrosis Visual Quantification Scale (HHVQS, e.g., HHVQSa or HHVQSp) for axillary and/or palmar
Hyperhidrosis Visual Analog Scale (HHVAS)
Dry Mouth Visual Analog Scale (DMVAS)
Dermatology-specific HRQOL as assessed by a modified Dermatology Life Quality Index
Dry Mouth Questions (Dry Mouth Severity/Incidence Questionnaire)
Transepidermal Water Vapor Loss (axillary and palmar)—Vapometer, Delfin Technologies, Kuopio Finland Study assessments were conducted at baseline (Day 1 of each treatment period), at the end of treatment (Day 21 of each treatment period), and at the End of Study (EOS) Visit (approximately at least 14 days following the last study drug administration). Subjects who completed the study treatment period between Days 21 and 28 were instructed to continue taking study treatment as prescribed until the "Day 21 Visit".

Dry mouth was not recorded as adverse events but only via the DMVAS and the dry mouth questions (Dry Mouth Severity/Incidence Questionnaire).

Subjects who discontinued study treatment early were asked to complete the EOS Visit approximately 14 days after the last study treatment administration. Subjects were monitored for safety and concomitant medication use at all visits.

Efficacy Measurements

Hyperhidrosis Disease Severity Scale (HDSS)

The HHDS is a tool for the assessment of disease severity in patients with PFH (Lowe, 2004; Strutton, 2004; Solish, 2005; Kowalski, 2006). The HDSS is a self-administered assessment in which the subject is asked to rate the severity of his/her hyperhidrosis by responding to the question "How would you rate the severity of your hyperhidrosis?" The scale has 4 scores from which to select
1. My sweating is never noticeable and never interferes with my daily activities
2. My sweating is tolerable but sometimes interferes with my daily activities
3. My sweating is barely tolerable and frequently interferes with my daily activities
4. My sweating is intolerable and always interferes with my daily activities These assessments were obtained as baseline (the beginning of each treatment period and at the end for each treatment period).

Hyperhidrosis Visual Quantification Scale (HHVQS)

Subjects with axillary hyperhidrosis were asked to complete the Hyperhidrosis Visual Quantification Scale for Axillary (HHVQSa) and subjects with palmar hyperhidrosis were asked to complete Hyperhidrosis Visual Quantification Scale for Palmer (HHVQSp). Subject with both axillary and palmar hyperhidrosis were to complete both assessments. These assessments were obtained as baseline (the beginning of each treatment period and at the end for each treatment period.

Axillary (HHVQSa)

Subjects were asked to quantify their axillary hyperhidrosis by responding to 2 directions:
1. Choose the picture that best described your worst experience over the past week.
2. Choose the picture that best describes your most common experience over the past week.

Figure 6:
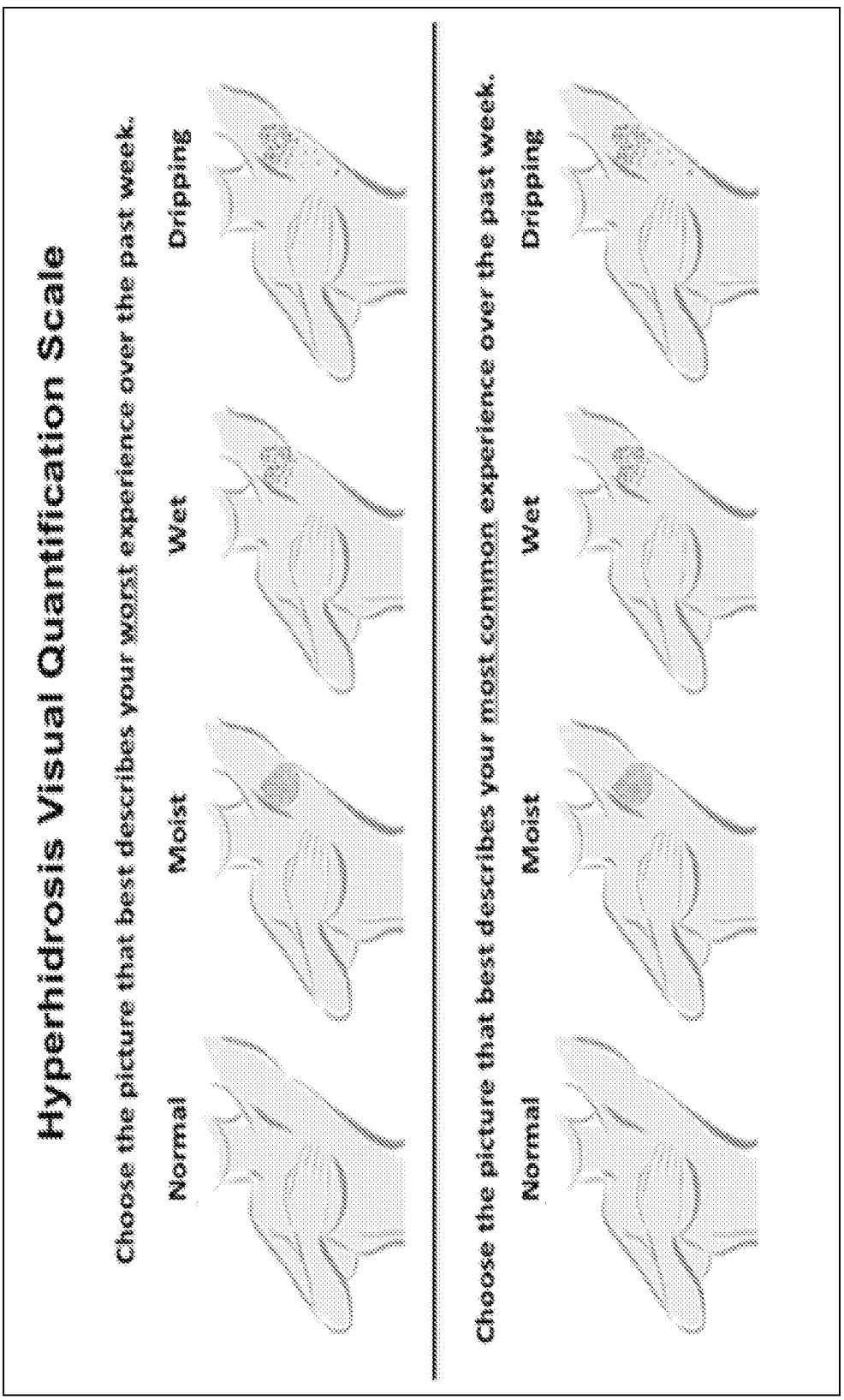
FIG. 6 depicts the axillary Hyperhidrosis Visual Quantification Scale (HHVQSa) used to assess treatment according to one embodiment.

Beneath each request, there were 4 descriptive diagrams of an axilla with the following captions:
1. Normal
2. Moist
3. Wet
4. Dripping FIG. 6 depicts the axillary Hyperhidrosis Visual Quantification Scale (HHVQSa).

Palmar (HHVQSp)

Subjects were asked to quantify their palmar hyperhidrosis by responding to 2 directions:
1. Choose the picture that best described your worst experience over the past week.

2. Choose the picture that best describes your most common experience over the past week.

Figure 7:
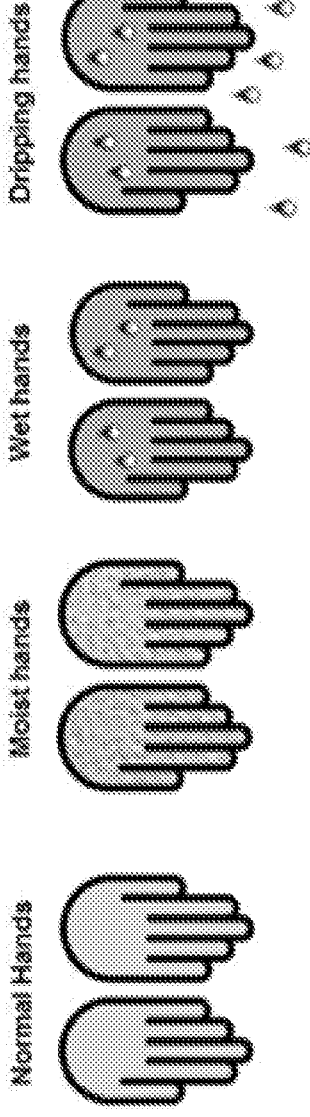
FIG. 7 depicts the palmar Hyperhidrosis Visual Quantification Scale (HHVQSp) used to assess treatment according to one embodiment.
Figure 7:
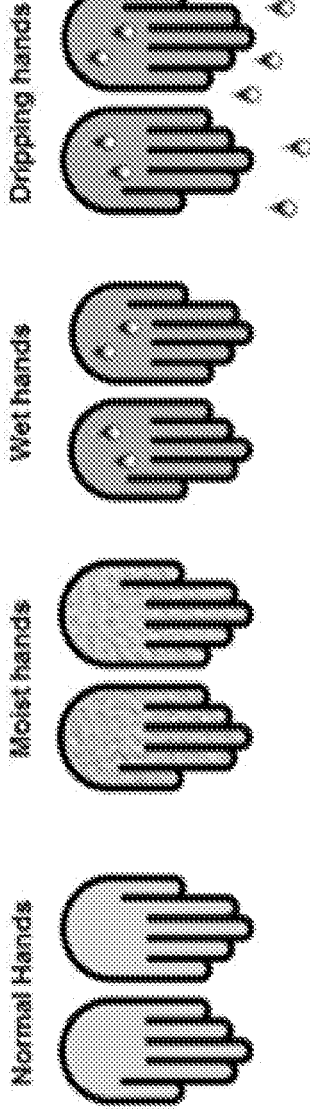

Beneath each request, there were 4 descriptive diagrams of a pair of hands with the following captions:
1. Normal Hands
2. Moist hands
3. Wet hands
4. Dripping hands FIG. 7 depicts the palmar Hyperhidrosis Visual Quantification Scale (HHVQSp).

Hyperhidrosis Visual Analog Scale (HHVAS)

Figure 8:
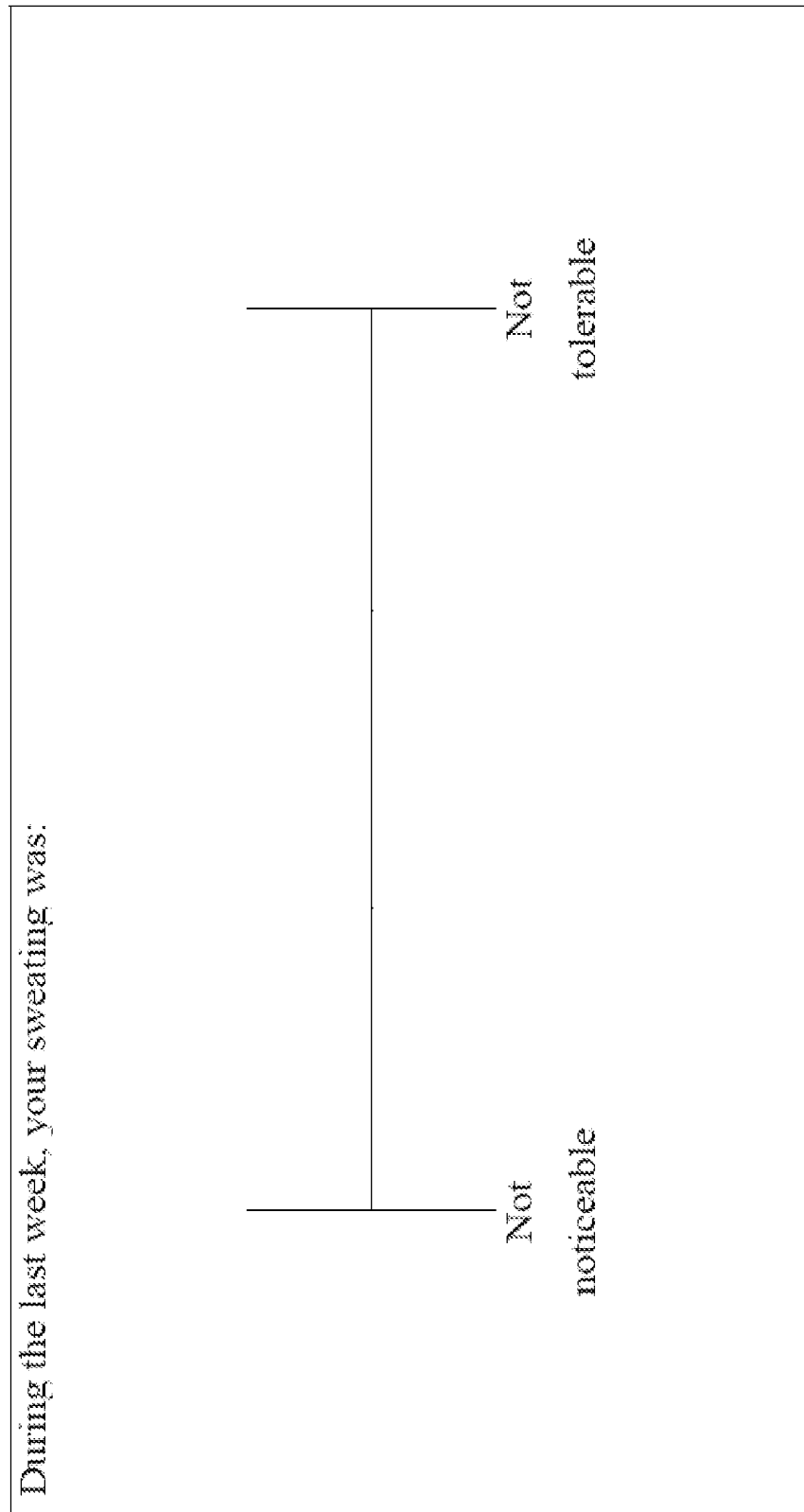
FIG. 8 depicts the Hyperhidrosis Visual Analog Scale (HHVAS) used to assess sweating according to one embodiment.

The HHVAS was used to quantify the severity of sweating in subjects during this clinical trial. Subjects will be instructed to indicate their level of disease severity by drawing a line through the continuous scale. The continuous scale was 100 mm in length. The score was determined by measuring the distance from the left anchor to where the line that the subject drew bisected the (100 mm) scale. The distance was measured and recorded in millimeters (mm). FIG. 8 depicts the Hyperhidrosis Visual Analog Scale used to assess sweating.

Dry Mouth Visual Analog Scale (DMVAS)

Figure 9:
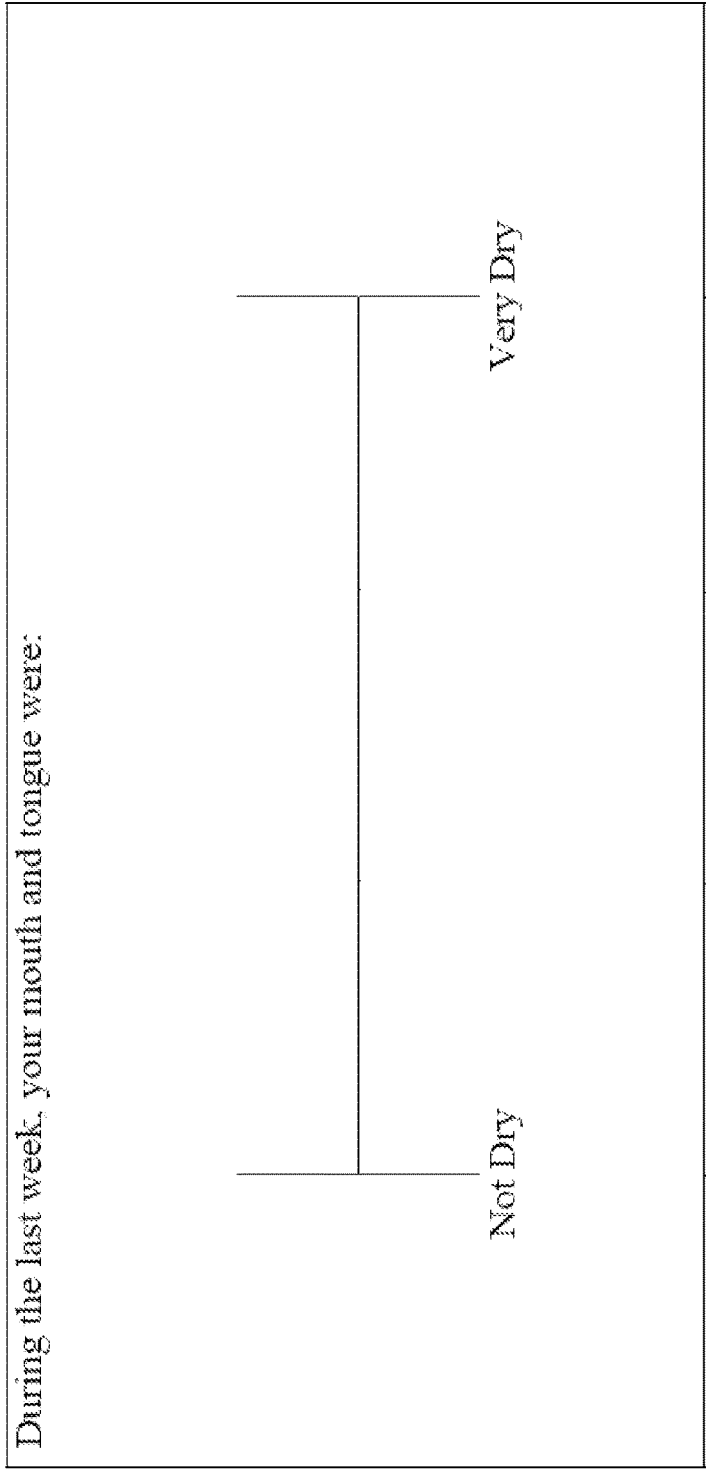
FIG. 9 depicts the Dry Mouth Visual Analog Scale used to assess dry mouth caused by administration of oxybutynin according to one embodiment.

The DMVAS will be used to quantify the severity of dry mouth experienced by subjects during this clinical trial. Subjects will be instructed to indicate their level of disease severity by drawing a line through the continuous scale. The score was determined by measuring the distance from the left anchor to where the line that the subject drew bisected the (100 mm) scale. The distance was measured and recorded in millimeters (mm). FIG. 9 depicts the Dry Mouth Visual Analog Scale used to assess dry mouth cause by administration of oxybutynin.

Dry Mouth Questions (Dry Mouth Severity/Incidence Questionnaire)

At the end of the end of each treatment period, investigational site staff questioned subjects regarding the incidence of dry mouth. This assessment occurred after the subject had completed the DMVAS and DTVAS and included questions relating to the incidence and severity of dry mouth symptoms and remedial actions taken. The investigator was instructed to query subjects in a non-judgmental, non-leading manner using the following script (© 2012, Thomas Tremblay and Robin Allgren) to elicit the incidence of dry mouth:

Have you had any dry mouth since starting (the most recent) study treatment? (at completion of Treatment Periods 1, 2, and 3)

If the subject indicated that dry mouth had occurred, the investigator was to qualify the dry mouth using the following script.

Which term: "mild", "moderate", or "severe" best describes the dry mouth you experienced?

Did you drink additional fluids to relieve your dry mouth?

Did you need to use hard candy or other types of lozenges to relieve your dry mouth?

Did you use any other types of products to moisten your mouth or relieve dryness?

On a scale of 0 to 10, with "0" being "not severe at all" and "10" being "the most severe imaginable", how would you rate the worst dry mouth that you experienced?

Gravimetric Testing

Gravimetric testing was used to quantify the amount of sweat produced by subjects prior to and following each study treatment.

Axillary Gravimetric Testing

Subjects with axillary hyperhidrosis were asked to refrain from application of topical antiperspirants and topical deodorants to the underarm region (bilateral) for the 24 hours prior to gravimetric testing. The evening prior to gravimetric testing, subjects were to shave the underarms and cleanse the areas thoroughly using a mild soap (e.g.; castile soap) to ensure that any residual deodorant or antiperspirant agent was removed.

If a subject had used antiperspirant within the 24 hours prior to planned axillary gravimetric testing, gravimetric testing was not performed and the subject was be re-instructed and rescheduled. Subjects in whom gravimetric testing was delayed continued to receive study drug per protocol until the rescheduled testing is completed.

If a subject neglected to shave and cleanse the underarms the evening before planned axillary gravimetric testing but did abstain from antiperspirant the underarms were shaved and cleaned prior to gravimetric testing and gravimetric testing was performed as scheduled.

Prior to gravimetric testing the axillary areas were completely dried using an absorbent non-lint producing fabric (e.g.; gauze sponge). Following drying of the axillae, a 4×6 inch absorbent cotton gauze pad (or equivalent) and the bag in which it is packaged was be weighed and the gauze was removed from the bag, folded in half and placed high in the axillary vaults and the subject was instructed to rest for 5 minutes with his/her arm(s) adducted to the torso with normal tension.

At the completion of 5 minutes, the gauze was to be removed, placed back in the same bag and weighed immediately. The difference in the weight of the gauze prior to the test and following the test was recorded.

Palmar Gravimetric Testing

Prior to gravimetric testing, subjects washed their hands using a mild soap and thoroughly dry the hands using an absorbent non-lint producing fabric (e.g.; gauze sponge or paper towels). Following drying of the hands, a pre-weighed cotton glove was placed on each of the hands of the subject and the cotton gloves were covered by pre-weighed nitrile gloves. The gloves were taped tightly around their wrists to prevent water loss. The subject was instructed to rest for 5 minutes with his/her hands in the gloves and down at their sides (to prevent water loss).

At the completion of 5 minutes, the cotton and nitrile gloves were removed and weighed immediately. The difference in the weight of the gloves prior to the test and following the test was recorded.

Transepidermal Water Vapor Loss

The Delfin VapoMeter (Delfin Technologies Ltd., Kuopio, Finland), a portable device that can measure water vapor loss through the skin, was used to evaluate the results of treating primary hyperhidrosis. It is a portable non-invasive instrument that has a closed measurement chamber that eliminates any interference from drafts (air conditioning and breathing, as well as the opening and closing of doors and windows), allowing accurate measurement of transepidermal water loss. The chamber contains relative humidity and temperature sensors.

To standardize the quantification of sweating, all subjects remained at rest for 20-30 minutes before the measurements in order to reduce external interference. The measurements were carried out in a temperature-controlled environment (21-24° C.).

For the measurements, the device was positioned perpendicular to the skin, remaining in contact with the skin surface until signaling that the reading was finished (generally 10 seconds). The evaporation rate was automatically calculated by the device on the basis of an increase in relative humidity in the closed chamber. This measurement expresses the increase in water mass (in g) in relation to the area of evaporation (in m$^2$) per unit of time (in h), the unit of measurement being therefore g/m2/h.

Axillary Transepidermal Water Vapor Loss

The device was placed perpendicular to the axillary skin at the top of the crease/fold and the arm will be closed. Transepidermal water loss assessments was conducted prior to gravimetric testing and on both axilla.

Palmar Transepidermal Water Vapor Loss

Measurements were carried out on the hypothenar region on both hands.

Modified Dermatology Life Quality Index (mDLQI)

The DLQI (Finlay, Kahn 1994) is a self administered assessment used to quantify the health-related quality of life of adults suffering from a skin disease and consists of 10 questions concerning the perception of the impact of skin diseases on different aspects of their health related quality of life over the last week. It has been validated for adult hyperhidrosis patients aged 16 years and older (Swartling 2001). For this study, the DLQI was modified to replace "skin" with "sweating" in the instructions and questionnaire items.

Clinical Study Population

Potential subjects were identified by outreach to local dermatologists who could refer their patients, by advertisement, and by a social media campaign. Subjects contacted the study center and were preliminarily screened via telephone interview and, if possibly eligible, were then evaluated in person. As mentioned above, potential subjects needed to demonstrate measurable anti-muscarinic induced dry mouth symptoms using the DMVAS. The study group included men and women age 18 to 70 with primary focal hyperhidrosis.

Subjects were included into the study based on the below inclusion criteria:

1. Able to provide written/signed informed consent.
2. Age 18 to 70 years old at time of informed consent.
3. Confirmed diagnosis of primary focal palmar and/or axillary hyperhidrosis.
4. Adequate renal and hepatic function defined as:
  a. Serum creatinine and estimated creatinine clearance <1.5×upper limit of normal range, and
  b. ALT or AST <1.5×upper limit of normal.
5. Negative serum pregnancy test for women of child bearing potential within the 7 days prior to the first study drug administration and willing to use an effective method of contraception for the duration of the clinical trial.
6. Willingness and ability to comply with the study protocol for the duration of the trial.
7. HDSS score of 3 or 4 at Visit 1.
8. A rating of 'wet hands' or "dripping hands" on the Hyperhidrosis Visual Quantification Scale (HHVQS) at Visit 1 for subjects with palmar hyperhidrosis.
9. Dry Mouth/Throat Visual Analog Scale (DM/TVAS) score of >25 mm at Visit 2.
10. A rating of "wet hands" or "dripping hands" on the Hyperhidrosis Visual Quantification Scale palmar (HHVQSp) for subjects with palmar hyperhidrosis or "wet" or "dripping" on the Hyperhidrosis Visual Quantification Scale axillary (HHVQSa) at Oxybutynin Run in Period Day −1 or Day −1 of Treatment Period 1 if they completed the Oxybutynin Run-In as a part of Study THVD 402 201
11. Dry Mouth Visual Analog Scale (DMVAS) score of 25 mm at Oxybutynin Run in Period Day 21. Subjects who participated in Study THVD 402 201 who have a documented DMVAS of at least 25 mm following the Oxybutynin Run-In period do not need to complete the open label oxybutynin run in period in this trial; these subjects can begin this trial with Treatment Period 1.

Subjects were excluded from the study based on the below exclusion criteria:

1. Contraindication to oxybutynin and/or pilocarpine including:
  a. Urinary retention or significant bladder outflow obstruction
  b. Gastric retention, gastrointestinal obstructive disorder (e.g., pyloric stenosis), or decreased gastric motility
  c. Narrow-angle glaucoma or acute iritis
  d. Myasthenia gravis
  e. Asthma, chronic bronchitis or COPD requiring pharmacological therapy
  f. Significant cardiovascular disease, including uncontrolled hypertension
  g. Known or suspected cholelithiasis or biliary tract disease
  h. Known or suspected renal colic or nephrolithiasis
  i. Previous hypersensitivity to pilocarpine or oxybutynin.
  j. Any other condition in which administration of oxybutynin or pilocarpine may pose a significant risk to the patient
2. Botox (onabotulinumtoxinA) treatment during the 8 months prior to screening or iontophoresis during the 2 months prior to screening.
3. History of local surgical excision of eccrine or apocrine glands of the axillae.
4. Any reason, in the opinion of the investigator that a subject would not be a reliable subject and provide accurate data.

All subjects will be warned against prolonged exposure to heat and/or sunshine.

Statistics

Efficacy and safety analyses were conducted on study treatment (THVD-102 [7.5/7.5], oxybutynin or placebo). Continuous data were summarized by using descriptive statistics (mean, SD, median, min, max) and categorical data were summarized in frequency tables. Using Day 1 of the first and each subsequent Treatment Period as baselines for measuring treatment effect, a Wilcoxon signed-rank test were performed. Safety analyses were performed in terms of the incidence and severity of adverse events. A p value of ≤0.05 was considered statistically significant. Primary comparisons of oxybutynin alone and THVD-102 [7.5/7.5] were made compared to placebo and each other in the following parameters:

Hyperhidrosis Disease Severity Scale (HDSS)
Gravimetric measurements (axillary and/or palmar)
Rate of water vapor loss using a closed chamber device
Hyperhidrosis Visual Quantification Scale (HHVQS)
Hyperhidrosis Visual Analog Scale (HHVAS)
Dry Mouth Visual Analog Scale (DMVAS)
Dry Mouth Questions (Dry Mouth Severity/Incidence Questionnaire)
Dermatology-specific HRQOL as assessed by a modified Dermatology Life Quality Index
Vital signs Overall Conclusions from Clinical Study
  THVD-102 [7.5/7.5] was generally well tolerated. No unexpected adverse effects were observed. The incidence and type of anti-muscarinic adverse effects was no greater than that which has been observed in prior trials of oxybutynin. There was no occurrence of a muscarinic adverse effect in the trial.

THVD-102 [7.5/7.5] was efficacious in the treatment of primary focal hyperhidrosis. There was a statistically significant effect in each of three measures of efficacy:
1) Hyperhidrosis Disease Severity Scale (p=0.03-0.05) THVD-102 [7.5/7.5]=1.06±1.11; Oxybutynin=1.33±1.03; placebo=0.5±0.62
1 point drop=50% reduction in sweating; 2 points=80% reduction
2) Hyperhidrosis Visual Analog Scale (p=0.01)
3) Hyperhidrosis Visual Quantification Scale (p=0.005-0.07)

The efficacy of THVD-102 [7.5/7.5] was not significantly different than that of oxybutynin in any of the categories.

Table 9 summarizes efficacy measurements by the above three measures.

TABLE 9

Measurements & p Values

| | HDSS PP | HDSS IT | HHVAS PP | HHVQSa PP (most common) | HHVQSa PP (worst) | HHVQSp PP (most common) | HHVQSp PP (worst) |
|---|---|---|---|---|---|---|---|
| n | 18 | 23 | 16 | 17 | 17 | 6 | 7 |
| THVD-102 [7.5/7.5] v. placebo | <0.05 | 0.03 | 0.002 | 0.005 | 0.007 | 0.07 | 0.04 |
| THVD-102 [7.5/7.5] v. Oxybutynin | 0.45 | 0.78 | 0.8 | 0.40 | 0.45 | 0.31 | 0.31 |

Figure 10:
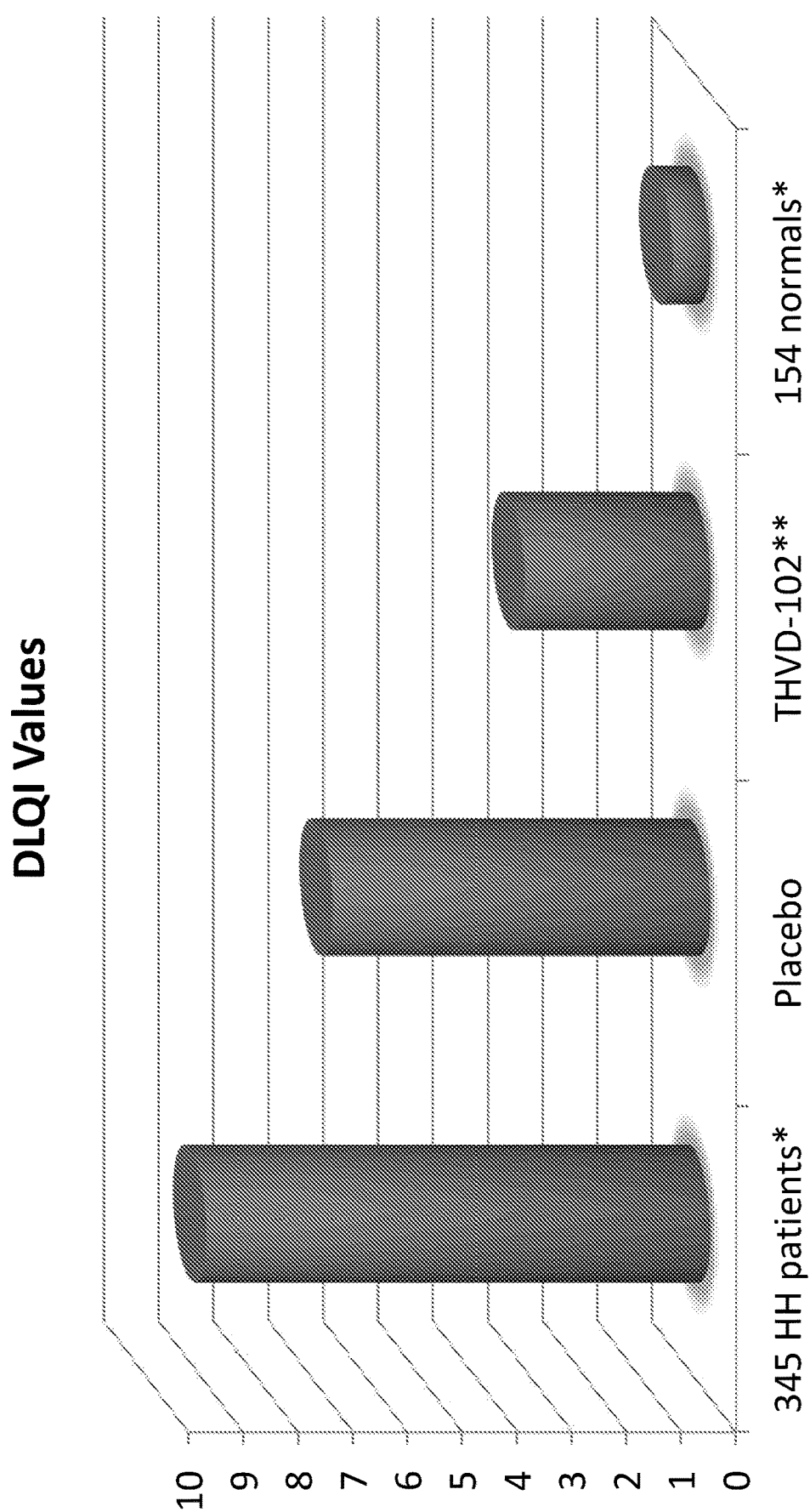
FIG. 10 depicts the improvement in quality of life as measured by a modified Dermatology Life Quality Index according to one embodiment.

THVD-102 [7.5/7.5] and oxybutynin resulted in a significant improvement in the quality of life (mDLQI) versus placebo (p<0.02 and p<0.04, respectively). The improvement in quality of life was not significantly different than that shown with oxybutynin (p=0.72). FIG. 10 depicts the improvement in quality of life by THVD-102 [7.5/7.5] as compared to placebo.

Using two different measurements, THVD-102 [7.5/7.5] showed a statistically significant reduction in dry mouth compared to oxybutynin. A significant reduction was shown in severity of dry mouth, using the Dry Mouth Visual Analog Scale (Table 10), and in the incidence of moderate to severe dry mouth using a questionnaire (Table 11). Incidence of none or mild vs. moderate or severe (THVD-102 [7.5/7.5] vs. oxybutynin p=0.02). Dry mouth visual analog scale (THVD-102 [7.5/7.5] vs. oxybutynin p=0.05)

TABLE 10

Dry mouth Visual Analog Scale, 100 mm scale, 100 = worst (PP)
Comparison of change in VAS Scores

| | Placebo | Oxybutynin | THVD-102 [7.5/7.5] |
|---|---|---|---|
| n | 18 | 18 | 18 |
| Change D0-D21 | 5.6 ± 26.7 | 43.9 ± 27.9 | 29.9 ± 31.0 |
| Actual Reduction | | −14.0 (p < 0.049) | |
| % Reduction | | 32% | |

TABLE 11

Questionnaire tool-incidence (PP)
None/mild vs moderate/severe dry mouth

| | Placebo | Oxybutynin | THVD-102 [7.5/7.5] |
|---|---|---|---|
| n | 18 | 18 | 18 |
| None/Mild | 16 (88%) | 5 (27%) | 10 (56%) |
| Moderate/Severe | 2 (11%) | 13 (72%) | 8 (44%) |
| Oxybutynin v. Placebo | | p < 0.0001 | |
| THVD-102 [7.5/7.5] v. Placebo | | p = 0.04 | |
| THVD-102 [7.5/7.5] v. Oxybutynin | | p = 0.02 | |

Although the foregoing disclosure has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the disclosure. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

What is claimed is:
1. A method of treating hyperhidrosis in a subject in need thereof, the method comprising:
orally administering to the subject once per day or twice per day a single unit dose of a therapeutically effective amount of a composition comprising an immediate release formulation of about 1 mg to 10 mg of oxybutynin, or a pharmaceutically acceptable salt thereof, and a delayed-immediate release formulation of about 1 mg to 10 mg of pilocarpine, or a pharmaceutically acceptable salt thereof.

2. The method according to claim 1, wherein the delayed-immediate release formulation of pilocarpine, or a pharmaceutically acceptable salt thereof, comprises a plurality of delayed-immediate release pilocarpine beads, wherein each pilocarpine bead comprises:
  a core;
  a first layer comprising pilocarpine, or a pharmaceutically acceptable salt thereof, positioned over the core; and
  a second layer comprising at least one polymer positioned over the first layer.

3. The method according to claim 1, wherein the composition is administered once per day.

4. The method according to claim 1, wherein the subject is diagnosed as having one or more condition selected from the group consisting of primary focal axillary hyperhidrosis, primary focal palmar hyperhidrosis, primary focal plantar hyperhidrosis, craniofacial hyperhidrosis, generalized hyperhidrosis, and compensatory sweating post-surgery.

5. The method according to claim 1, wherein the composition administered contains about 4 mg of the oxybutynin, or pharmaceutically acceptable salt thereof, and pilocarpine, or a pharmaceutically acceptable salt thereof, in an amount selected from the group consisting of about 4 mg, about 6 mg, and about 9 mg.

6. The method according to claim 1, wherein the composition administered contains about 6 mg of the oxybutynin, or pharmaceutically acceptable salt thereof, and pilocarpine, or a pharmaceutically acceptable salt thereof, in an amount selected from the group consisting of about 4 mg, about 6 mg, and about 9 mg.

7. The method according to claim 1, wherein the composition administered contains about 9 mg of the oxybutynin, or pharmaceutically acceptable salt thereof, and pilocarpine, or a pharmaceutically acceptable salt thereof, in an amount selected from the group consisting of about 4 mg, about 6 mg, and about 9 mg.

8. The method according to claim 1, wherein the composition comprises oxybutynin hydrochloride (HCl) and pilocarpine hydrochloride (HCl).

9. The method according to claim 1, wherein the composition is formulated such that the peak plasma concentration of the oxybutynin, or a pharmaceutically acceptable salt thereof, and the peak plasma concentration of the pilocarpine, or a pharmaceutically acceptable salt thereof, occurs at approximately the same time.

10. The method according to claim 2, wherein the first layer comprises a polymer selected from the group consisting of cellulose, hydroxyethylcellulose, hydroxypropylcellulose, hydroxypropylmethylcellulose, carboxymethylcellulose, maltodextrin, sucrose, modified starch, a salt of alginic acid, soluble gums, carrageenan, polyvinylpyrrolidone (PVP) or polyvinylpolypyrrolidone (PVPP), ethylcellulose, cellulose acetate phthalate, hydroxypropylmethylcellulose phthalate, insoluble gums, polymethacrylate, a polyvinyl alcohol, shellac, and polyvinyl acetate phthalate.

11. The method according to claim 10, wherein the first layer comprises hydroxypropylmethylcellulose.

12. The method according to claim 2, wherein the second layer comprises one or more polymers selected from the group consisting of cellulose, hydroxyethylcellulose, hydroxypropylcellulose, hydroxypropylmethylcellulose, carboxymethylcellulose, maltodextrin, sucrose, modified starch, a salt of alginic acid, soluble gums, carrageenan, polyvinylpyrrolidone (PVP) or polyvinylpolypyrrolidone (PVPP), ethylcellulose, cellulose acetate phthalate, hydroxypropylmethylcellulose phthalate, insoluble gums, polymethacrylate, a polyvinyl alcohol, shellac, and polyvinyl acetate phthalate.

13. The method according to claim 12, wherein the second layer comprises ethylcellulose and hydroxypropylcellulose.

14. The method according to claim 13, wherein the ratio of hydroxypropylcellulose to ethylcellulose is from about 5:1 to about 1:5 by weight.

15. The method according to claim 14, wherein the ratio of hydroxypropylcellulose to ethylcellulose is about 1:1 by weight.

16. The method according to claim 2, wherein the core is about 15% to about 40% of the total weight of the bead,
  the first layer is about 5% to about 30% of the total weight of the bead, and
  the second layer is about 40% to about 70% of the total weight of the bead.

17. The method according to claim 2, wherein the core is a microcrystalline core that is about 20% of the total weight of the bead;
  the first layer comprises the pilocarpine, or a pharmaceutically acceptable salt thereof, in an amount that is about 8% of the total weight of the bead, hydroxypropyl methylcellulose in an amount that is about 8% of the total weight of the bead, and talc in an amount that is about 4% of the total weight of the bead; and
  the second layer comprises ethylcellulose in an amount that is about 26% of the total weight of the bead, hydroxypropylcellulose in an amount that is about 26% of the total weight of the bead, and dibutyl sebacate in an amount that is about 5% of the total weight of the bead.

18. The method according to claim 2, wherein the plurality of delayed-immediate release pilocarpine beads are formulated such that 20% or less of pilocarpine, or a pharmaceutically acceptable salt thereof, is released approximately 20 minutes after administering to the subject, and about 75% or more of pilocarpine, or a pharmaceutically acceptable salt thereof, is released approximately 30 minutes thereafter.

* * * * *